(12) United States Patent
Omar et al.

(10) Patent No.: US 7,858,768 B2
(45) Date of Patent: Dec. 28, 2010

(54) DETECTION AND DISTINGUISHING INFECTIOUS BURSAL DISEASE VIRUS (IBDV) STRAINS BY MOLECULAR BIOLOGY METHOD

(75) Inventors: Abdul Rahman Omar, Ehsan (MY); Mohd Hair-Bejo, Ehsan (MY); Ideris Aini, Ehsan (MY); Hairul Aini Binti Hamzah, Ehsan (MY)

(73) Assignee: Universiti Putra Malaysia, Ehsan (MY)

( * ) Notice: Subject to any disclaimer, the term of this patent is extended or adjusted under 35 U.S.C. 154(b) by 0 days.

(21) Appl. No.: 12/551,969

(22) Filed: Sep. 1, 2009

(65) Prior Publication Data

US 2009/0325149 A1     Dec. 31, 2009

Related U.S. Application Data

(62) Division of application No. 11/268,341, filed on Nov. 7, 2005, now Pat. No. 7,659,066.

(30) Foreign Application Priority Data

Nov. 5, 2004   (MY) .............................. PI20044610

(51) Int. Cl.
*C07H 21/04* (2006.01)
*C12Q 1/68* (2006.01)
(52) U.S. Cl. ...................... 536/24.33; 435/6
(58) Field of Classification Search ............... 536/22.1; 435/6, 91.2
See application file for complete search history.

(56) References Cited

U.S. PATENT DOCUMENTS

2005/0214316 A1* 9/2005 Brown .................... 424/186.1
2006/0099574 A1   5/2006 Omar

OTHER PUBLICATIONS

Lowe et al. A computer program for selection of oligonucleotide primers for polymerase chain reactions. Nucleic Acids Research, vol. 18, No. 7, pp. 17571761, 1990.*
Ayyadevara, S. et al., "Discrimination of Primer 3'-Nucleotide Mismatch by *Taq* DNA Polymerase during Polymerase Chain Reaction," *Analytical Biochemistry* 2000; 284:11-18.
Akin, A. et al., "Chemiluminescent detection of infectious bursal disease virus with a PCR-generated nonradiolabeled probe," *J. Vet Diagn Invest* 1993; 5:166-173.
Aldea, C. et al., "Rapid Detection of Herpes Simplex Virus DNA in Genital Ulcers by Real-Time PCR Using SYBR Green I Dye as the Detection Signal," *Journal of Clinical Microbiology* Mar. 2002; 40(3):1060-1062.
Banda, A. et al., "Molecular Characterization of Infectious Bursal Disease Virus from Commercial Poultry in the United States and Latin America," *Avian Diseases* 2003; 47:87-95.

Bayliss, C. D. et al., "A comparison of the sequences of segment A of four infectious bursal disease virus strains and identification of a variable region in VP2," *Journal of General Virology* 1990; 71:1303-1312.
Beuret et al., "Simultaneous detection of enteric viruses by multiplex real-time RT-PCT," *J. Virol Methods* 2004; col. 115, pp. 1-8.
Bonnet, G. et al., "Thermodynamic basis of the enhanced specificity of structured DNA probes," *Proc. Natl. Acad. Sci. USA* May 1999; 96:6171-6176.
Buck et al., "Design Strategies and Performance of Custom DNA Sequencing Primers," *Biotechnicques* 1999; 27(3):528-536.
Burkhardt, E. et al., "Susceptibility of Chicken Blood Lymphoblasts and Monocytes to Infectious Bursal Disease Virus (IBDV)," *Arch Virol* 1987; 94:297-303.
Cosgrove, A.S., "An apparently new disease of chickens—avian nephrosis," Dec. 1961, Avian Dis. 6:385-389, 1962, p. 385.
Cao, Y. C. et al., "Molecular Characterization of Seven Chinese Isolates of Infectious Bursal Disease Virus: Classical, Very Virulent, and Variant Strains," *Avian Diseases* 1998; 42(2):340-351.
Chai, Y. F. et al., "Characterisation of New Zealand isolates of infectious bursal disease virus," *Arch Virol* 2001; 146:1571-1580.
Davis, V. S. et al., "Adapting the Polymerase Chain Reaction to a Double-Stranded RNA Genome," *Analytical Biochemistry* 1990; 189:30-34.
De Monbrison, F. et al., "Real-time PCR for chloroquine sensitivity assay and for *pfmdrl-pfcrt* single nucleotide polymorphisms in *Plasmodium falciparum,*" *Journal of Microbiological Methods* 2003; 54:391-401.
Desjardin, L. E. et al., "Comparison of the ABI 7700 Systems (TaqMan) and Competitive PCR for Quantification of IS6110 DNA in Sputum during Treatment of Tubercolosis," *Journal of Clinical Microbiology* Jul. 1998; 36(7):1964-1968.
Eterradossi, N. et al., "Critical amino acid changes in VP2 variable domain are associated with typical and atypical antigenicity in very virulent infectious bursal disease viruses," *Arch Virol* 1998; 143:1627-1636.
Gibson, U. E. M et al., "A Novel Method for Real Time Quantitative RT-PCR," *Genome Research* 1996; 6:995-1001.
Heid, C. A. et al., "Real time quantitative PCR," *Genome Res.* 1996; 6:986-994.
Higuchi, R. et al., "Kinetic PCR Analysis: Real-time Monitoring of DNA Amplification Reactions," *Bio/Technology* 1993; 11:1026-1030, Abstract.

(Continued)

*Primary Examiner*—Suryaprabha Chunduru
(74) *Attorney, Agent, or Firm*—Wolf, Greenfield & Sacks, P.C.

(57) ABSTRACT

The present invention relates to a novel method to detect and differentiate different strains of infectious bursal disease virus (IBDV) in a chicken and other bird sample. RNA was obtained from said samples by using a pair of primer (Primer FVVC & RVVC) in a reverse transcriptase-polymerase chain reaction. Two different primer combinations (Primer IF & IVIR) and (Primer IF & RCLA) and real-time polymerase chain reaction conditions were designed and optimized for rapid differentiation of very virulent and vaccine strains of IBDV based on detection of signatory threshold cycle (Ct) and melting temperature (Tm) values.

25 Claims, 21 Drawing Sheets

OTHER PUBLICATIONS

Hoque, M. M. et al., "Pathogenicity of SspI-positive infectious bursal disease virus and molecular characterization of the VP2 hypervariable region," *Avian Pathology* 2001; 30:369-380.

Hoque, M. M. et al., "Sequence and Phylogenetic Analysis of the VP2 Gene of Very Virulent Infectious Bursal Disease Virus Isolates," *J Biochem Mol Biol Biophys.* 2002; Apr; 6(2):93-9.

Ismail, N. M. et al., "Lack of Pathogenicity of Five Serotype 2 Infectious Bursal Disease Viruses in Chickens," *Avian Diseases* 1988; 32:757-759.

Jackwood, D. J. et al., "Enzyme-Linked Immunosorbent Assay-Based Detection of Antibodies to Antigenic Subtypes of Infectious Bursal Disease Viruses of Chickens," *Clinical and Diagnostic Laboratory Immunology* Jul. 1996; 3(4):456-463.

Jackwood, D. J. et al., "Identification of Infectious Bursal Disease Virus Quasispecies in Commercial Vaccines and Field Isolates of This Double-Stranded RNA Virus," *Virology* 2002; 304:105-113.

Jackwood, D. J. et al., "Real-Time Reverse Transcriptase-Polymerase Chain Reaction Detection and Analysis of Nucleotide Sequences Coding for a Neutralizing Epitope on Infectious Bursal Disease Viruses," *Avian Diseases* 2003; 47:738-744.

Jackwood, D. J. et al., "Restriction Fragment Length Polymorphisms in the VP2 Gene of Infectious Bursal Disease Viruses," *Avian Diseases* 1997; 41:627-637.

Jackwood, D. J. et al., "Restriction Fragment Length Polymorphisms in the VP2 Gene of Infectious Bursal Disease Viruses from Outside the United States," *Avian Diseases* 1999; 43(2):310-314.

Jackwood, D. J. et al., "Detection of Infectious Bursal Disease Viruses in Commercially Reared Chickens Using the Reverse Transcriptase/Polymerase Chain Reaction-Restriction Endonuclease Assay," *Avian Diseases* 1997; 41:137-143, Abstract.

Jackwood et al., "Infectious bursal disease virus and proventriculitis in broiler chickens," *Avian Diseases* 2003; 47:681-690.

Kibenge, F. S. B. et al., "Biochemistry and Immunology of Infectious Bursal Disease Virus," *J. Gen Virol.* 1988; 69:1757-1775.

Lasher, H. N. et al., "Infectious bursal disease," *World's Poultry Science Journal* 1994; 50:133-166, Abstract.

Liu, J. et al., "Antigenic and molecular characterization of recent infectious bursal disease virus isolates in China," *Virus Genes* 2002; 24(2):135-147.

Liu, H.-J. et al., "Detection of genetic variations in serotype I isolates of infectious bursal disease virus using polymerase chain reaction and restriction endonuclease analysis," *Journal of Virological Methods* 1994; 48:281-291.

Lowe et al., "A computer program for selection of oligonucleotide primers for polymerase chain reactions," *Nucleic Acids Research* 1990; 18(7):1757-1761.

Lukert and Saif, "Infectious Bursal Disease" in: Diseases of Poultry, Y.M. Saif, Ed., 11th ed., Iowa State University Press, Ames, Iowa, Chapter 6, pp. 161-179, 2003.

Mackay, I. M. et al., "Survey and Summary: Real-time PCR in virology," *Nucleic Acids Research* 2002; 30(6):1292-1305.

Majó, N. et al., "Molecular characterization of Spanish infectious bursal disease virus field isolates," *Avian Diseases* 2002; 46:859-868.

McNulty, M.S. et al., "Antigenic Relationship of Non-Serotype 1 Turkey Infectious Bursal Disease Viruses from the United State and United Kingdom," *Avian Diseases* Apr.-Jun. 1988; 32(2):374-375, Abstract.

Moody, A. et al., "Measuring infectious bursal disease virus RNA in blood by multiplex real-time quantitative RT-PCR," *Journal of Virological Methods* 2002; 85:55-64.

Morrison, T.B. et al., "Quantification of low-copy transcripts by continuous SYBR® Green I monitoring during amplification," *BioTechniques*; 1998; 24(6):954-962, Abstract.

Nicolas, L. et al., "Real-time PCR for detection and quantitation of *Leishmania* in Mouse Tissues," *Journal of Clinical Microbiology* May 2002; 40(5):1666-1669.

Peters, A. et al., "Infectious bursal virus polyprotein expression arrests growth and mitogenic stimulation of B lymphocytes," *Arch Virol.* 2004; 149:2413-2426.

Petek, M. et al., "Biological and physico-chemical properties of the infectious bursal disease virus (IBDV)," *Avian Pathology* 1973; 2(2):135-152.

Ririe, K. M. et al., "Product differentiation by analysis of DNA melting curves during the polymerase chain reaction," *Analytical Biochemistry* 1997; 245:154-160.

Rosenberger, J. K. et al., "The Effects of Age, Route of Exposure, and Coinfection with Infectious Bursal Disease Virus on the Pathogenicity and Transmissibility of Chicken Anemia Agent (CAA)," *Avian Diseases* 1989; 33:753:759, Abstract.

Rudd, M. F. et al., "Characterisation of an Indonesian very virulent strain of infectious bursal disease virus," *Arch Virol* 2002; 147:1303-1322.

Sapats, S. I. et al., "Antigenic and sequence heterogeneity of infectious bursal disease virus strains isolated in Australia," *Arch Virol* 2000; 145:773-785.

Shcherbakova, L. O. et al., "Comparative analysis of the VP2 variable region," *Mol. Gen. Mikrobiol. Virusol.* 1998; 1:35-40, Abstract.

Shu et al., "Development of Group- and Serotype-Specific One-Step SYBR Green I-Based Real-Time Transcription-PCR Assay for Dengue Virus," *J. Clin. Microbiol.* 2003; 41(6):2408-2416.

Snyder, D. B. "Changes in the field status of infectious bursal disease virus," *Avian Pathology* 1990; 19(3):419-423.

Tham, K. M. et al., "Detection of infectious bursal disease virus by reverse transcription-polymerase chain reaction amplification of the virus segment A gene," *Journal of Virological Methods* 1995; 53:201-212.

Ture, O. et al., "Restriction Fragment Length Polymorphism Analysis of Highly Virulent Strains of Infectious Bursal Disease Viruses from Holland, Turkey, and Taiwan," *Avian Diseases* 1998; 42:470. 479, Abstract.

Van Den Berg, T. P. "Acute infectious bursal disease in poultry: a review," *Avian Pathology* 2000; 29:175-194.

Waterfall, C. M. et al., "Kinetic characterisation of primer mismatches in allele-specific PCR: a quantitative assessment," *Biomedical and Biophysical Research Communications* 2002; 299:715-722.

Wittwer, C. T. et al., "The LightCycler™: A microvolume multisample fluorimeter with rapid temperature control," *BioTechniques*; Jan. 1997; 22:176-181.

Wu, C. C. et al., "Molecular detection of infectious bursal disease virus by polymerase chain reaction," *Avian Disease* 1992; 36:221-226.

Zierenberg, K. Z. et al., "Rapid identification of "very virulent" strains of infectious bursal disease virus by reverse transcription-polymerase chain reaction combined with restriction enzyme analysis," *Avian Pathology* 2001; 30:55-62.

Zorman-Rojs, O. et al., "Very virulent infectious bursal disease virus in Southeastern Europe," *Avian Diseases* 2003; 47:186-192.

\* cited by examiner

|  |  | 2133 |  |  |  |  | 2150 |  |  |
|---|---|---|---|---|---|---|---|---|---|
|  |  | ↓ |  |  |  |  | ↓ |  |  |
| [c]Primer IVIR | [a]2131 | GAC | GTG | AAC | ACC | GGG | TCC | AAC | 2151 |
|  | 710 | D | V | N | T | G | S | N | 716 |
| [d]Primer RCLA | [a]2131 | GAT | GTA | AAC | ACC | GGG | CCC | AAC | 2151 |
|  | 710 | D | V | N | T | G | P | N | 716 |

Figure 1

Figure 2A
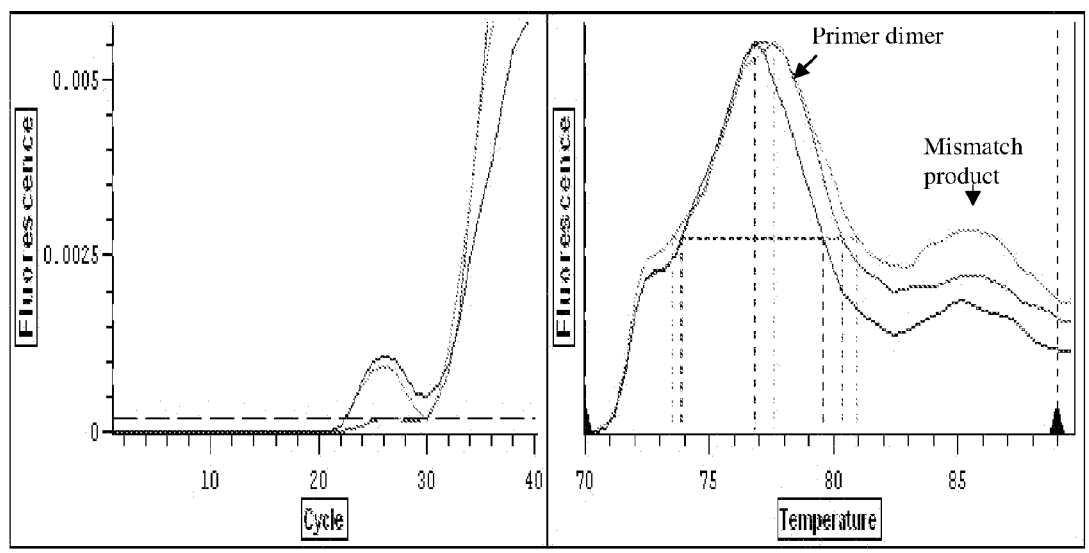
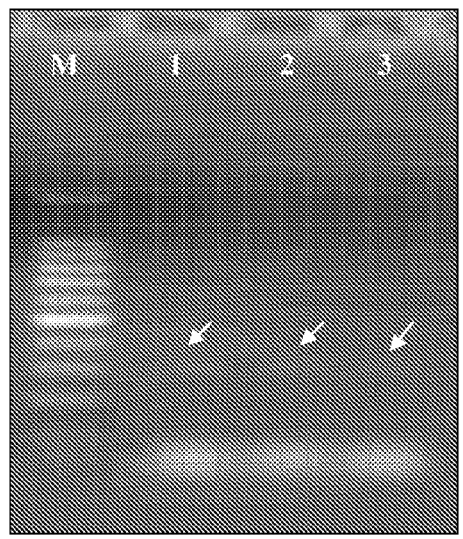
Figure 2B

Figure 9A
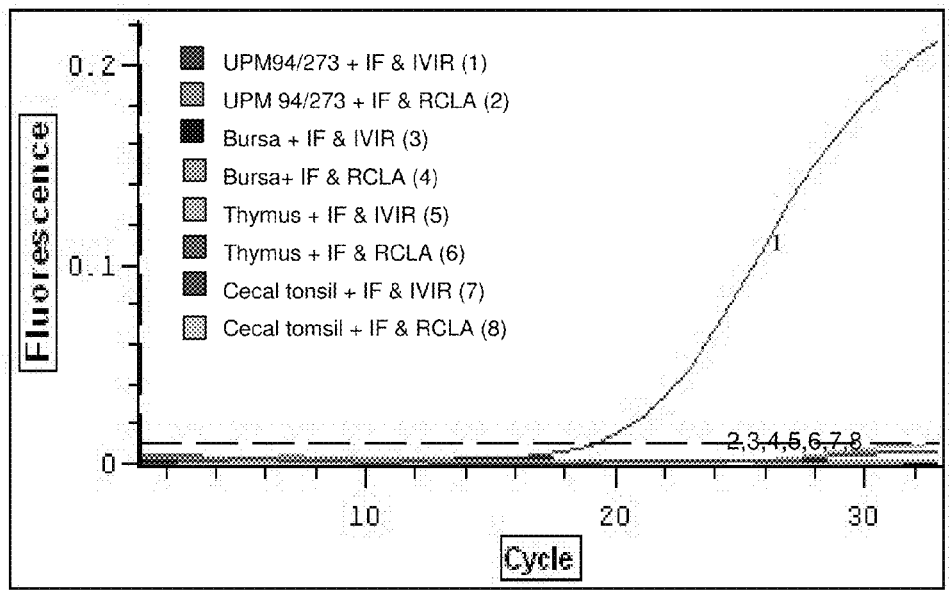
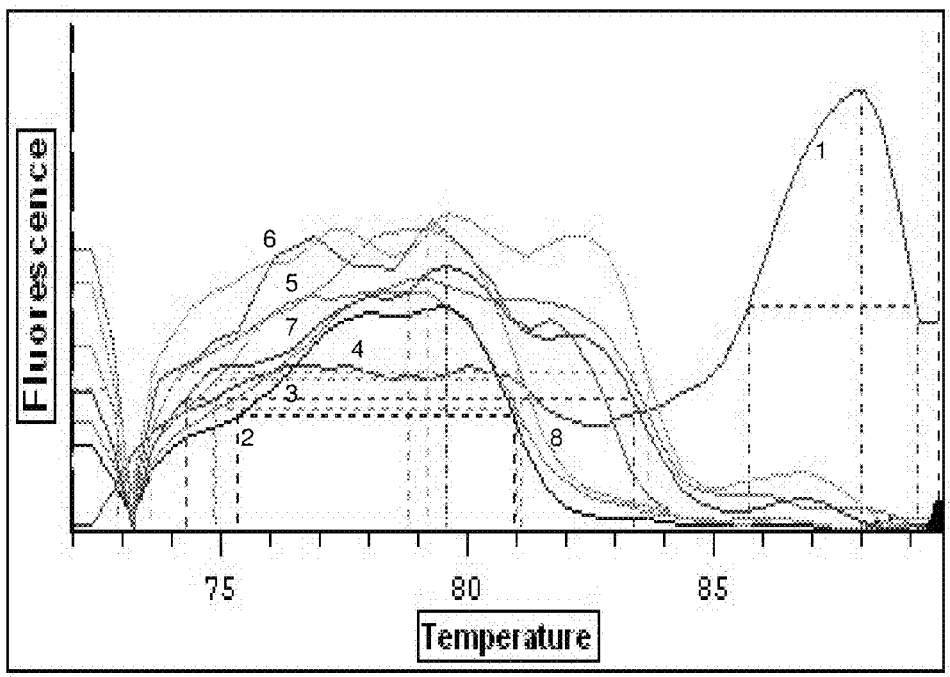
Figure 9B

```
                          10        20        30        40        50        60
                 ....|....|....|....|....|....|....|....|....|....|....|....|
PrimerIF    ATGCTCCAGATGGGGTACTTC----------------------------------------
PrimerIVIR  --------------------------------------------------------------
Primer RCLA --------------------------------------------------------------
UPM97/61    ..............................T......G.....................
UPM94/273   ..............................T......G.....................
D78         ............................................................
TAD         ............................................................
LZD         ............................................................
IBDVAC      ....................T.........................T.............
OKYM        ..............................T..T...G.....................
UK661       ..............................TT.....G.....................
IBDKS       ..............................T......G.....................
D6948       ..............................T......G.....................
BD3/99      ..............................T......G.....................
Tasik94     ..............................T......G.....................
Chinju      ..............................T......G.....................
HK46        ..............................T......G.....................
SH95        .........C....................T......G.....................
Gx          ..............................T......G.....................
SDH1        .........C....................T......G.....................
T09         ....................T.........T......G.....................
GZ9112      ............................................................
D78         ............................................................
CU-1M       ............................................................
P2          ............................................................
CT          ............................................................
CEF94       ............................................................
PBG-98      ............................................................
JD1         .........G..................................................
HZ2         .........G..................................................
Edgar       ............................................................
```

Figure 10

```
                    130       140       150       160       170       180
               ....|....|....|....|....|....|....     ....|....|....|....|....|....|
PrimerIF       --------------------------------------------------------------------
PrimerIVIR     --------------------------------------------------------------------
PrimerRCLA     --------------------------------------------------------------------
UPM97/61       ....C...................................A..........................
UPM94/273      ....C...................................A..........................
D78            ...............T.................................................A......
TAD            ...............T.................................................A......
LZD            ..................................................................T.......
IBDVAC         .......C.................................AT................................
OKMY           ....C...................................A..........................
OKMYT          ....C...................................A................A.........
UK661          G...C................................................................
IBDKS          .....A........A......................................................
D6948          ....C................................................................
BD3/99         ....C................................................................
Tasik94        ....C................................................................
Chinju         ....C................................................................
HK46           ....C....C...........................................................
SH95           ....C................................................................
Gx             ......................................................................
SDH1           ....C................................................................
T09            ......................................................................
GZ9112         ...............A.....................................................
D78            ...............T.................................................A......
CU-1M          ...............T.................................................A......
P2             ...............T.................................................A......
CT             ...............T.................................................A......
CEF94          ...............T.................................................A......
PBG-98         ...............T.................................................A......
JD1            ...............T.................................................A......
HZ2            ...............T.................................................A......
Edgar          .......C..............................................................
```

Figure 10 (continued)

```
                    190       200       210       220       230       240
                 ....|....|....|....|....|....|....|....|....|....|....|....|
PrimerIF         ------------------------------------------------------------
PrimerIVIR       ------------------------------------------------------------
PrimerRCLA       ------------------------------------------------------------
UPM97/61         .........A............C..C.A.................C..G...........
UPM94/273        ......................C..C.A.................C..G...........
D78              ....T.......................................................
TAD              ....T.......................................................
LZD              ....T.......................................................
IBDVAC           .T.......A............C..C..G..........................C....
OKYM             .A....................C..C.A.................C..G...........
UK661            .........A............C..C.A.................T..G...........
IBDKS            ......................C..C.A.................C..G...........
D6948            ......................C..C.A.................C..G...........
BD3/99           ......................C..C.A................GC..G...........
Tasik94          ......................C..C.A.................C..G...........
Chinju           ......................C..C.A.................C..G...........
HK46             ......................C..C.A.................C..G...........
SH95             ......................C..C.A.................C..G...........
Gx               ......................C..C.A.................C..G...........
SDH1             ......................C..C.A.................C..G...........
T09              .........................C.A.................T..G......C....
GZ9112           ......................C.....................................
D78              ....T.......................................................
CU-1M            ....T.......................................................
P2               ....T.......................................................
CT               ....T.......................................................
CEF94            ....T.......................................................
PBG-98           ....T.......................................................
JD1              ....T.......................................................
HZ2              ....T.......................................................
Edgar            .........A...................................A..............
```

```
                        250        260        270        280        290        300
                   ....|....|....  ....|....|....|....|....|....|....|....|....|
Primer IF          ------------------------------------------------------------
Primer IVIR        ----------------------------------------------------------CG
Primer RCLA        ----------------------------------------------------------TG
UPM97/61           ........................C...................C.....T....
UPM94/273          .........................-.................T-....T....
D78                ..........T..................T.G........................T.
TAD                ..........T..................T..........................T.
LZD                ..........T..................T..........................T.
IBDVAC                                                 T..G ..C..T..T
OKY                .......................................T.....T....
UK661              .......................................T.....T....
IBDVKS             .......................................T.....T....
D6948              .......................................T.....T....
BD3/99             .......................................T.....T....
Tasik94            .......................................T.....T....
Chinju             .......................................T.....T....
HK46               ................T......................T.....T....
SH95               ...........................A........T..T.....T....
SH/92              .......................................T.....T....
Gx                 .......................................T.....T....
SDH1               ...........................A........T..T.....T....
T09                ................T..............................T....
GZ9112             ...........A..C........G................................T.
D78                .............................T..........................T.
CU-1M              .............................T..........................T.
P2                 .............................T..........................T.
CT                 ..........T..................T.G........................T.
CEF94              .............................T..........................T.
PBG-98             .............................T..........................T.
JD1                .............................T..........................T.
HZ2                .............................T..........................T.
Edgar              .............................T..........................T.
```

```
                              310
                   ....|....|....|.
Primer IF          ----------------
Primer IVIR        TGAACACCGGGTCCAA
Primer RCLA        TAAACACCGGGCCCAA
UPM97/61           .G........T.....
UPM94/273          .G........T.....
D78                ................
TAD                ................
LZD                ................
IBDVAC             ........T.......
OKYM               .G........T.....
UK661              .G........T.....
IBDKS              .G........T.....
D6948              .G........T.....
BD3/99             .G........T.....
Tasik94            .G........T.....
Chinju             .G........T.....
HK46               .G........T.....
SH95               .G........T.....
Gx                 .G........T.....
SDH1               .G........T.....
T09                .G........T.....
GZ9112             ................
D78                ................
CU-1M              ................
P2                 ................
CT                 ................
CEF94              ................
PBG-98             ................
JD1                ................
HZ2                ................
Edgar              ................
```

Figure 10 (continued)

SEQUENCE LISTING

<160> NUMBER OF SEQ ID NOS: 6

<210> SEQ ID NO 1
<211> LENGTH: 18
<212> TYPE: DNA
<213> ORGANISM: Artificial
<220> FEATURE:
<223> OTHER INFORMATION: oligonucleotide primer

<400> SEQUENCE: 1
agagggtgcc acgctatt                                                       18

<210> SEQ ID NO 2
<211> LENGTH: 19
<212> TYPE: DNA
<213> ORGANISM: Artificial
<220> FEATURE:
<223> OTHER INFORMATION: Oligonucleotide primer

<400> SEQUENCE: 2
ggtactggcg tcctgcatt                                                      19

<210> SEQ ID NO 3
<211> LENGTH: 21
<212> TYPE: DNA
<213> ORGANISM: Artificial
<220> FEATURE:
<223> OTHER INFORMATION: Oligonucleotide primer

<400> SEQUENCE: 3
atgctccaga tggggtactt c                                                   21

<210> SEQ ID NO 4
<211> LENGTH: 18
<212> TYPE: DNA
<213> ORGANISM: Artificial
<220> FEATURE:
<223> OTHER INFORMATION: Oligonucleotide primer

<400> SEQUENCE: 4
ttggacccgg tgttcacg                                                       18

<210> SEQ ID NO 5
<211> LENGTH: 18
<212> TYPE: DNA
<213> ORGANISM: Artificial
<220> FEATURE:
<223> OTHER INFORMATION: Oligonucleotide primer

<400> SEQUENCE: 5
ttgggcccgg tgtttaca                                                       18

<210> SEQ ID NO 6
<211> LENGTH: 7
<212> TYPE: PRT
<213> ORGANISM: Infectious bursal disease virus

<400> SEQUENCE: 6

Ser Trp Ser Ala Ser Gly Ser
1               5

DETECTION AND DISTINGUISHING INFECTIOUS BURSAL DISEASE VIRUS (IBDV) STRAINS BY MOLECULAR BIOLOGY METHOD

RELATED APPLICATION

This application is a divisional of U.S. application Ser. No. 11/268,341, filed Nov. 7, 2005, and now pending, the entire disclosure of which is incorporated by reference herein.

FIELD OF THE INVENTION

This invention relates to the detection and distinguishing Infectious Bursal Disease Virus (IBDV) strains by a Molecular Biology Method in chicken or other birds. More particularly, this invention relates to distinguishing different Infectious Bursal Disease Virus (IBDV) strains in chicken and other bird sample by Real-time Polymerase Chain Reaction (PCR) method.

BACKGROUND OF THE INVENTION

Infectious bursal disease (IBD) is an acute contagious viral disease of young chickens often known as Gumboro disease (Kibenge et al., J Gen Virol. 69(Pt 8):1757-1775, 1988; Lasher et al., Avian Dis. 41(1):11-19, 1997). The etiological agent, IBD virus (IBDV), has a predilection for the cells of the bursa of Fabricius where the virus infects actively dividing and differentiating lymphocytes of the B-cell lineage (Burkhardt et al., Arch Virol. 94(3-4):297-303, 1987). Thus, IBD is a fatal immunosuppressive disease causing heavy losses to the poultry industry (Eterradossi et al., Arch Virol. 143(8):1627-1636, 1998).

The first outbreak of IBDV was reported in commercial chicken flocks in Delaware, USA (Cosgrove, Avian Dis. 6:385-389, 1962). The IBDV strains, which were isolated during the outbreak, now referred to as classical serotype I isolates. The disease was also first report in Europe in 1962 (Faragher, Vet. Bull. 42:361-369, 1972). And from 1966 to 1974, IBD was reported in the Middle East, Southern and Western Africa, India, the Far East and Australia (Faragher, 1972; Firth, Aust Vet J. 50(3):128-130, 1974; Jones, N Z Vet J. 34(3):36, 1986; van den Berg, Avian Pathol. 29:175-194, 2000). In most cases, the IBDV strains that associated with the outbreaks were of low virulence and caused only 1 to 2% of specific mortality (van den Berg, 2000).

However, a new IBDV strain (antigenic variant) emerged and able to cause up to 5% specific mortality in USA (Rosenberger and Cloud, Avian Dis. 33(4):753-759, 1989). The antigenic variant was recovered from flocks with selection pressure of field vaccination against classical IBDV serotype I (Snyder, 1990). Although being antigenic variant these isolates have only minor amino acid changes and do not form a separate serotype.

Nevertheless, these changes occur at the VP2 conformation-dependent antigenic epitopes that are responsible for stimulating virus neutralizing antibodies (Bayliss et al., J Gen Virol. 71(Pt 6):1303-1312, 1990). Currently, variant form of IBD has been reported outside Central America particularly in countries such as China (Cao et al., Avian Dis. 42(2):340-351, 1998), South America (Banda et al., Avian Dis. 47(1): 87-95, 2003) and Australia (Sapats and Ignjatovic, Arch Virol. 145(4):773-785, 2000).

Since variant IBDV causes only changes at the bursa and depending on the immune status of the chickens, the disease is often manifested with subclinical signs, it is difficult to detect variant IBDV in commercial flocks. Hence, variant IBDV may be common in many countries in the world but remains undiagnosed. A second serotype—serotype II of IBDV was identified in 1987 (McNulty and Saif, Avian Dis. 132(2):374-375, 1988). Serotype II IBDV isolates are apathogenic and are recovered mainly from turkeys (Ismail et al., Avian Dis. 32(4):757-759, 1988).

In the 1990s, IBDV isolates, which were able to break through levels of maternal antibodies that normally were protective, were reported in Europe (Chettle et al., Vet Rec. 125(10):271-272, 1989). These isolates, the so called very virulent IBDV are causing more severe clinical signs during an outbreak which mortality approaching 100% in susceptible flocks, and are now found almost world-wide (van den Berg, 2000). The emergence of very virulent strains of IBDV has complicated the immunization programs against the disease.

Early vaccination may result in failure due to interference with the maternal antibody, whilst its delay may cause field virus infections. Currently, outbreaks of vvIBDV have been reported throughout various countries in the world (Banda et al., Avian Dis. 47(1):87-95, 2003; Cao et al., Avian Dis. 42(2):340-351, 1998; Chai et al., Arch Virol. 146(8):1571-1580, 2001; Chettle et al., 1989; Eterradossi et al., Zentralbl Veterinarmed B. 39(9):683-691, 1992; Hoque et al., J Biochem Mol Biol Biophys. 6(2):93-99, 2002; Liu et al., Virus Genes. 24(2):135-147, 2002; Majo et al., Avian Dis. 46(4): 859-868, 2002; Rudd et al., Aust Vet J. 81(3):162-164, 2003; Scherbakova et al., 1998; Ture, et al., Avian Dis. 42(3):470-479, 1998; Zorman-Rojs et al., Avian Dis. 47(1):186-192, 2003).

In designing an effective disease control program one should consider the diagnostic methods use to diagnose disease caused by infectious agent. Currently, IBD can be diagnosed based on virus isolation, electron microscopy, immunofluorescence, virus neutralization, monoclonal antibody assays, and/or enzyme-linked immunosorbent assay (Jackwood et al., Clin Diagn Lab Immunol. 3(4):456-463, 1996; Jackwood et al., Avian Dis. 40(2):457-460, 1996; Liu et al., J Virol Methods. 48(2-3):281-291, 1994; Lukert and Saif, Infectious bursal disease. In: Diseases of Poultry, 10th edn (Eds. Calnek et al.), Iowa State University Press, Ames, Iowa, pp. 721-738, 1997; Wu et al., Avian Dis. 36(2):221-226, 1992). However, these methods have one or more disadvantages such as time consuming, labour intensive, expensive and of low sensitivity (Wu et al., 1992).

Recently, the reverse transcriptase polymerase chain (RT-PCR) has been used to detect IBDV based on the amplification of the central hypervariable region of the VP2 region (Tham et al., J Virol Methods. 53(2-3):201-212, 1995; Jackwood and Nielsen, Avian Dis. 41(1):137-143, 1997). Subsequently, RT-PCR assay followed by restriction fragment length polymorphism (RFLP) also has been used to detect and differentiate IBDV strains (Jackwood and Sommer, Avian Dis. 41(3):627-637, 1997; Jackwood and Sommer, Avian Dis. 43(2):310-314, 1999; Hoque et al., Avian Pathol. 30:369-380, 2001; Ture et al., Avian Dis. 42(3):470-479, 1998; Zierenberg et al., 2001).

Although, this method able to differentiate different IBDV strains, it is not automated and time consuming. Both radioactive and non-radioactive based nucleic acid probes that can differentiate IBDV strains have been used in the detection of IBDV (Akin et al., Vet Diagn Invest. 5(2):166-173, 1993; Davis and Boyle, Avian Dis. 34(2):329-335, 1990). However, apart for academic interest, their use in diagnosing IBD is uncommon.

Fluorescence-based real-time PCR assays have been developed to provide a rapid and sensitive method for quantifying nucleic acids (Gibson et al., Genome Res. 6(10):995-1001, 1996; Heid et al., Genome Res. 6(10):986-994, 1996; Desjardin et al., J Clin Microbiol. 36(7):1964-1968, 1998). In this assay, reactions are monitored by the point in time during cycling when amplification of a PCR product is first detected rather than the amount of PCR product accumulated after a fixed number of cycles. There are currently 2 general approaches in real-time PCR depending on the types of fluorescence dyes. The simplest method uses fluorescent dye, SYBR Green I that bind specifically to double stranded DNA (Morrison et al., Biotechniques. 24(6):954-958, 960, 962, 1998). The major problem with SYBR Green I-based detection is that non-specific amplifications cannot be distinguished from specific amplifications. However, specific amplification can be verified by melting curve analysis (Ririe et al., Anal Biochem. 245(2):154-160, 1997).

The other dyes (TaqMan, Molecular Beacons, Scorpion) rely on the hybridization of fluorescence labeled probes to the correct amplicon (Wittwer et al., Biotechniques. 22(1):130-131, 134-138, 1997; Bonnet et al., 1999). Accumulation of PCR products is detected by monitoring the increase in fluorescence of the reporter dye. The threshold cycle (Ct) is defined as the fractional cycle number at which the reporter fluorescence generated by the accumulating amplicons passes a fixed threshold above baseline (Mackay et al., Nucleic Acids Res. 30(6):1292-1305, 2002).

Hence, a plot of the log of initial target copy number for a set of standards versus Ct is a straight line whereby the higher the starting copy number of the nucleic acid target, the sooner a significant increase in fluorescence is observed (Higuchi et al., Biotechnology (NY). 11(9):1026-1030, 1993; Gibson et al., 1996; Heid et al., 1996; Desjardin et al., 1998). It has also been established that primers combination playing an important role for the Ct value prediction, where the approach is similar to the analysis of single-nucleotide polymorphism (Frederique et al., 2003; Christy et al., 2002; Srinivas et al., 2000). Thus, several recent studies have used SYBR Green I based real-time PCR to differentiate different serotypes or strains of organisms based on Ct and/or Tm values (Aldea et al., J Clin Microbiol. 40(3):1060-1062, 2002; Beuret, J Virol Methods. 115(1):1-8, 2004; Nicolas et al., J Microbiol Methods. 51(3):295-299, 2002; Shu et al., J Clin Microbiol. 41(6):2408-2416, 2003). A quantitative real-time PCR assay based on TaqMan has been developed to detect IBDV (Moody et al., J Virol Methods. 2000 85(1-2):55-64, 2000). In other recent studies by Jackwood and Sommer (Virology. 304(1):105-113, 2002) and Jackwood et al. (Avian Dis. 47(3):738-744, 2003), TaqMan based real-time PCR was shown to be able to detect vaccine and wild type IBDV strains in infected chickens. However, the assay is expensive and more complex compared to the method established in this study. In addition, the application of the method to differentiate very virulent and vaccine strains IBDV is not known.

SUMMARY OF THE INVENTION

The biological material, which is to be investigated, was obtained in some suitable matter and isolated. By means of standardized methods, RNA was isolated from the material. A defined amount of RNA was transcribed into cDNA by means of conserved primers in RT reaction. Subsequently, a defined amount of cDNA was used to generate specific products using PCR.

One of the most common dyes that bind to double-stranded DNA that is commonly used in real-time PCR is SYBR Green I. In real-time PCR, measurements are detected during the exponential phase of the reaction typically by obtaining the threshold cycle (Ct) value. Ct value can be defined as the fractional cycle number at which there is a significant increase in fluorescence above a specified threshold.

The Ct value is also proportional to the numbers of target copies present in the samples. In SYBR Green I based real-time PCR the specificity of the amplification is determined by measuring the melting temperature (Tm) of the product in melting curve analysis. Different IBDV strains can be differentiated based on the Ct values by using different primer combinations and the detection of expected Tm confirm the specificity of the amplification.

The PCR conditions are optimized in order to obtain effective PCR parameters on the ingredients and profiles using samples containing IBDV RNA in a SYBR Green I based real-time PCR. Hence, for differentiation of very virulent from vaccine strains of IBDV by using Primer IF & IVIR and Primer IF & RCLA, a PCR product from very virulent strain IBDV has an early amplification (Ct value between 19 to 28 and Tm between 86° C. to 88° C.) and late amplification (Ct value>29 and Tm<82° C.) or no amplification (Ct value 0 and Tm<82° C.), respectively.

Meanwhile, differentiation of vaccine from very virulent strains of IBDV by using Primer IF & IVIR and Primer IF & RCLA, the PCR product from vaccine strain of IBDV has an early amplification (Ct value between 19 to 28 and Tm between 86° C. to 88° C.) and late amplification (Ct value>29 and Tm<82° C.) or no amplification (Ct value 0 and Tm<82° C.), respectively.

It is an objective of the invention to provide a new method for differentiating IBDV strains and for identifying IBDV strains based on the detection of signatory Ct and Tm values.

BRIEF DESCRIPTION OF THE DRAWINGS

FIG. 1 depicts nucleotide sequences and the deduced amino acids translation of primers IVIR and RCLA. For primer IVIR, the nucleotide sequence and amino acid sequence corresponds to SEQ ID NO:7 and SEQ ID NO:8 respectively. For primer RCLA, the nucleotide sequence and amino acid sequence corresponds to SEQ ID NO:9 and SEQ ID NO:10 respectively. The IVIR primer matched to very virulent strains meanwhile primer RCLA matched to vaccine strains. [a]The nucleotide sequences of the primers that associated with amino acid variations are bold. [c]The primer conserved to very virulent strains, UPM97/61 (AF247006), UPM94/273 (AF527039), OKYM (D49706), UK661 (X92760), IBDKS (L42284), D6948 (AF240686), BD3/99 (AF362776), Tasik94 (AF322444), Chinju (AF508176), HK46 (AF092943), SH95 (AF13474), Gx (AY 444873), SDH1 (AY323952) and TO9 (AY099456). [d]The primer conserved to vaccine (attenuated) strains, D78 (AF499929), Cu-1M (AF362771), P2 (X84034), CT (AJ310185), CEF94 (AF194428), PBG-98 (D00868), JD1 (AF321055), HZ-2 (AF321054) and Edgar (AF462026).

FIG. 2A shows the influence of the number of cycles in real-time PCR assay using template from vaccine strain D78 and mismatch primer combinations. FIG. 2B shows evidence of faint PCR product of the expected size (316 bp) (arrow) and primer-dimer from amplification of D78 cDNA with mismatch primer combinations (IF & IVIR) after 33 cycles. The Tm of the mismatch product was 86° C. to 87° C. whilst the Tm for the dimer product was 77° C. Lane M, 100 bp marker (Promega, USA), Lane 1, 2 and 3 are triplicate of D78 with primers IF & IVVR.

FIG. 9 depicts the specificity of real-time PCR using IF & IVIR and IF & RCLA primer combinations on control uninfected tissue samples. No specific amplifications were detected using IF & IVIR and IF & RCLA primers combinations on ~4,000 ng/μl of total RNA extracted from bursa, thymus and cecal tonsil of control uninfected SPF-chickens. As expected the positive control sample, UPM94/273 showed specific amplification using match primer IF and IVIR. No amplification from the negative control tissue and the Tm values ranged between 72.0° C. to 79.6° C.

DETAILED DESCRIPTION OF THE INVENTION

Figure 3A:
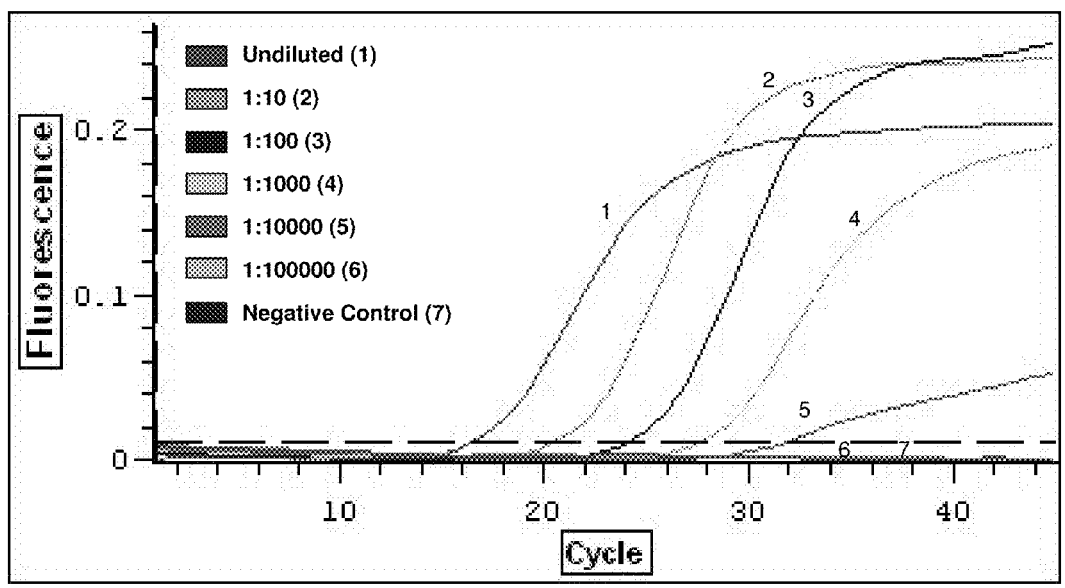
FIG. 3 shows the performance of the real-time in detecting very virulent strain UPM94/273. Reverse transcription was generated from 12,000 ng/μl of total RNA. The real-time PCR was performed using 10-fold dilutions from $10^0$ to $10^{-5}$ (7,700 ng/μl to 0.077 ng/μl) of cDNA template (UPM94/273), match primer combination (primer IF & IVIR), mismatch primer combination (primer IF & RCLA), 1 μl of SYBR Green I (diluted 1:$10^3$) as labeling dye and fluorescence threshold limit set at 0.01. Amplification of PCR product using match primer was detected from undiluted until $10^{-3}$ diluted cDNA whilst amplification using mismatch primer was detected only from undiluted cDNA (FIGS. 3A and 3C). With match primer combinations, the Tm of amplicons from undiluted to $10^{-3}$ diluted cDNA was between 87.2° C. to 87.6° C. whilst the Tm for $10^{-4}$ to $10^{-5}$ diluted cDNA and negative control ranged from 78° C. to 78.4° C. Melting curve analysis also showed that the mismatch primer combinations produced a product with Tm of 87.6° C. from undiluted cDNA whilst the Tm for $10^{-1}$ until $10^{-5}$ diluted cDNA and negative control was 81.6° C.
(FIG. 3D). A standard curve derived from 10-fold diluted cDNA of very virulent IBDV strain indicated a linear relationship was observed between the amount of input cDNA and the Ct value. The regression equation was Ct=3.7765 (log 10 dilution)+16.393 and $R^2$=0.999 (FIG. 3E).

The field of the invention is detection of IBDV in homogenate tissue samples using different primer combinations. Total RNA from test sample is reverse transcribed using a pair of conserved primer. The RT product is amplified using different primer combinations where by, different IBDV strains can be differentiated based the detection of Ct and Tm values. Based on these principals, a pair of primer, primers FVVC & RVVC that hybridized to the conserved region are designed and used in RT reaction.

The RT products are then used as template in cDNA amplification using 2 pairs of primers whereby only the sequences of the reverse primers are different depending on the strains of IBDV; primers IF & IVIR and primers IF & RCLA each are specific to very virulent and vaccine strains of IBDV, respectively. Since the concentration of cDNA influence the specificity of the assay, the optimum of cDNA concentration is optimized. In addition, other parameters including concentration of total RNA, primers, MgCl$_2$, SYBR Green I, PCR profiles and standardization of the fluorescence threshold level of the real-time PCR machine were also optimized.

Hence, for differentiation of very virulent from vaccine strains of IBDV primer IF & IVIR and primers IF & RCLA are used. A PCR amplification product from very virulent strain IBDV has an early amplification (Ct value between 19 to 28 and Tm between 86 to 88° C.) and late amplification (Ct value>29 and Tm<82° C.) or no amplification (Ct value 0 and Tm<82° C.), respectively. The invention describes the development of a novel SYBR Green I based real-time PCR method for the detection of very virulent and vaccine strains of IBDV based on detection of signatory Ct and Tm values.

Thus, this invention also includes novel real-time PCR-based assays which do not require size determination of the PCR amplification product to confirm the specific amplification of the IBDV target nucleic acid sequence. Therefore, the invention includes simple format assays which obviate the need for complex molecular biology techniques such as restriction enzyme digestion and sequencing to confirm that the amplification product is, indeed, of IBDV strains of very virulent or vaccine strains. The methods of the invention are, therefore, less prone to operator error, faster, and may be fully automated. In describing and claiming the present invention, the following terminology will be used in accordance with the definitions set out below.

As used herein, "nucleic acid," "RNA," "cDNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

The term "very virulent" strain of IBDV means samples containing IBDV that associated with high mortality in chickens and with the following characteristic amino acid residues at the positions 222 (alanine), 242 (isoleucine), 256 (isoleucine) and 294 (isoleucine) of the VP2 region, at the positions 680 (tyrosine), 685 (asparagine), 715 (serine) and 751 (aspartate) of the VP4 region and at the positions 990 (valine) and 1005 (alanine) of the VP3 region. Typically, a very virulent IBDV usually associated with mortality up to 100% in SPF chickens, 25% mortality in broilers and 60% in layers.

The term "vaccine" strain of IBDV means samples containing IBDV that do not cause mortality in non-vaccinated commercial chickens and with the following characteristic amino acid residues at VP2 region; 253 (histidine), 279 (asparagine), and 284 (threonine) and associated with one or more changes at the serine residues of the heptapeptide region SWSASGS (SEQ ID NO:6) at the position 326 to 332. A vaccine strain also has characteristic amino acid residues at the positions 680 (cysteine), 685 (lysine), 715 (proline) and 751 (histidine) of the VP4 region and at the positions 990 (alanine) and 1005 (threonine) of the VP3 region. Typically, a vaccine strain is an attenuated classical IBDV derived from repeated passages in embryonated eggs and/or cell cultures.

As used herein, "effective amount" means an amount sufficient to produce a selected effect. For example, an effective amount of cDNA is an amount sufficient to amplify a segment of nucleic acid by PCR provided that a DNA polymerase, buffer, template, and other conditions, including temperature conditions, known in the art to be necessary for practicing PCR are also provided.

The term "test sample" as used herein, means anything suspected of containing a target sequence. The test sample can be derived from any biological source and can be used (i) directly as obtained from the source or (ii) following a pre-treatment to modify the character of the sample. The pre-treatment that can be applied for example, disrupting cells, preparing liquids from solid materials, diluting viscous fluids, filtering liquids, concentrating liquids, inactivating interfering components, adding reagents, purifying nucleic acids, and the like. Typically, the test sample will be derived from bursal tissue samples.

A "target sequence" as used herein means a nucleic acid sequence that is detected, amplified, or otherwise is complementary to one of the primers herein provided.

A "match primer" as used herein means the nucleotide sequence of primer with at least the last 3 nucleotide sequences at the 3'end conserved to the template sequences. Typically, a match primer will has a conserved nucleotide sequences with template sequences.

A "mismatch primer" as used herein means the nucleotide sequence of primer with at least the last 1 nucleotide sequence at the 3'end differ to the template. Typically, a mismatch primer will has 1 to 3 nucleotide variation at the 3'end with the template sequences.

The term "bp" means base pair.

The term "signatory Ct and Tm values" means consistent readings that give selected or desirable effect; to distinguish different strains of IBDV, i.e., very virulent from vaccine strain. Typically, a match primer and template combination will give an early amplification (Ct value between 19 to 28 and Tm between 86° C. to 88° C.) and late amplification (Ct value>29 and Tm<82° C.) or no amplification (Ct value 0 and Tm<82° C.). A mismatch primer and template combination will give late amplification (Ct value>29 and Tm<82° C.) or no amplification (Ct value 0 and Tm<82° C.).

DETAILED EXAMPLE OF APPLICATION

Isolation of Very Virulent and Vaccine Strains

A total of 6 IBDV which include 2 field isolates of very virulent strains (UPM97/61 and UPM94/273) and 4 vaccine strains (Table 1) were used. The very virulent viruses were in the form of bursal homogenate whilst the vaccine strains were distilled in 8 to 10 ml of deionised water and used for RNA extraction.

TABLE 1

Infectious bursal disease viruses used in the study

| Isolates | Strains |
| --- | --- |
| UPM97/61 | very virulent |
| UPM94/273 | very virulent |
| D78 | vaccine |
| TAD Gumboro | vaccine |
| Delvax Gumboro LZD | vaccine |
| IBDVAC | vaccine |

Primer Design

Five different primers were used in this study (Table 2). All the primers were designed with the aid of Primer Premier 5.0 software. The primers were designed based on the following criteria for real-time PCR; primers should be designed to amplify short amplicons. Minimum length of the amplicons should be 80 bp and not exceed 400 bp. Ideally, primers should have about 50% of G/C content. The nucleotide difference should be at the 3'end region of the primers and the region should have no more than two G and/or C bases.

TABLE 2

Primers used for amplification of different strains of IBDV. The nucleotide variations between the primers are indicated in bold.

| Primer | Sequence (5'-3') | Positions[a] | SEQ ID NO |
|---|---|---|---|
| FVVC[d] | AGA GGG TGC CAC GCT ATT | 1662-1679 | SEQ ID NO: 1 |
| RVVC[d] | GGT ACT GGC GTC CTG CAT T | 2255-2237 | SEQ ID NO: 2 |
| IF[d] | ATG CTC CAG ATG GGG TAC TTC | 1835-1855 | SEQ ID NO: 3 |
| IVIR[b] | TTG GAC CCG GTG TTC ACG | 2150-2133 | SEQ ID NO: 4 |
| RCLA[c] | TTG GGC CCG GTG TTT ACA | 2150-2133 | SEQ ID NO: 5 |

[a]The numbering of the nucleotide position based on Bayliss et al. (1990).
[b]The sequences of the primer was conserved when compared to very virulent strains, UPM97/61 (AF247006), UPM94/273 (AF527039), OKYM (D49706), UK661 (X92760), IBDKS (L42284), D6948 (AF240686), BD3/99 (AF362776), Tasik94 (AF322444), Chinju (AF508176), HK46 (AF092943), SH95 (AF13474), Gx (AY 444873), SDH1 (AY323952) and TO9 (AY099456).
[c]The sequences of the primer was conserved when compared to vaccine (attenuated) strains, D78 (AF499929), Cu-1M (AF362771), P2 (X84034), CT (AJ310185), CEF94 (AF194428), PBG-98 (D00868), JD1 (AF321055), HZ-2 (AF321054) and Edgar (AF462026).
[d]The sequences of the primers were conserved when compared to both very virulent and attenuated vaccine strains of IBDV as stated above.

The primers FVVC and RVVC were designed from the conserved region of VP4 of both very virulent and vaccine strains to generate a 593 bp product. Similar to primers FVVC & RVVC, primer IF was also designed from the conserved region of VP4 of both very virulent and attenuated vaccine strains whilst primers IVIR and RCLA were designed based on conserved sequences of very virulent and attenuated vaccine strains, respectively, and expected to amplify a 316 bp product.

Primers IVIR and RCLA differed by 3 nucleotide differences at positions 2133, 2136 and 2146 (Table 2). The relationship between the primer combinations and IBDV isolates as template is indicated in Table 3. The primers IF and IVIR were considered as match primer combination for very virulent strains but as mismatch primer combination for vaccine strains. Meanwhile, primers IF and RCLA were considered as match primer combination for vaccine strains but as mismatch primer combination for very virulent strains.

TABLE 3

Primer combinations and their relationship to template (IBDV isolates) used in real-time PCR.

| Isolates | Origin | Strains | Primer combinations[a] | Relationship between primer combinations to IBDV |
|---|---|---|---|---|
| UPM97/61 | UPM | very virulent | IF & IVIR | Match |
|  |  |  | IF & RCLA | Mismatch |
| UPM94/273 | UPM | very virulent | IF & IVIR | Match |
|  |  |  | IF & RCLA | Mismatch |
| D78 | Intervet | vaccine | IF & IVIR | Mismatch |
|  |  |  | IF & RCLA | Match |
| TAD Gumboro | Lohman | vaccine | IF & IVIR | Mismatch |
|  |  |  | IF & RCLA | Match |
| Delvax Gumboro LZD | Mycofarm | vaccine | IF & IVIR | Mismatch |
|  |  |  | IF & RCLA | Match |
| IBDVAC | Veterinary Research Institute | vaccine | IF & IVIR | Mismatch |
|  |  |  | IF & RCLA | Match |

[a]The forward primer (IF) is conserved whilst the reverse primers (IVIR and RCLA) varies depending on the strains of IBDV.

As shown in FIG. 1, the nucleotide difference at position 2146 associated with an amino acid substitution at position 715.

RNA Extraction. Total RNA was extracted from the prepared biological material using Tri Reagent® (Life Technologies, USA) following the method described by the manufacturer.

Reverse Transcriptase

The extracted RNA was transcribed into cDNA using primers FVVC and RVVC. In this study, two tubes format of real-time PCR was carried out. The optimum conditions of the PCR reaction and programs were optimized using IBDV strains, UPM94/273 and D78 each represent the very virulent and vaccine strains, respectively. Briefly, a premix reaction containing 5,000 ng/μl to 13,000 ng/μl of total RNA, 25 pmole of primers FVVC & RVVC, 1 μl of DMSO (v/v) in a 10 μl volume was incubated at 99° C. for 5 mins. The premix reaction was reverse transcribed at 42° C. for 1 hour in a final volume of 20 μl containing 2× of reaction buffer (Promega, USA), 2 μl of 10 mM dNTP mixture, 5.0 U of AMV reverse transcriptase, 20 U of recombinant Rnasin ribonuclease inhibitor. The reaction was then denatured at 99° C. for 1 min to inactivate the reverse transcriptase. The cDNA was then chilled on ice for 5 mins and was used immediately or stored at −80° C.

Determination of the RNA and cDNA Concentration and Purity

The concentration and purity of the extracted total RNA and cDNA were measured at the wavelength of 260 nm and 280 nm using a spectrophotometer.

Optimization of the Real-Time PCR

The condition of the real-time PCR was optimized by using different concentration of cDNA and SYBR Green I. Briefly, cDNA (undiluted to 1:10$^5$ dilution) was used as template was made in 50 μl volume with the following ingredients; 3.0 mM MgCl$_2$, 2 μl of 10 mM dNTP mixture, 25 pmole/μl of each primer (Primer IF & IVIR and Primer IF & RCLA), 2.5 U of Taq DNA polymerase (Promega, USA), 1 μl of SYBR Green 1 dye diluted 1:10$^3$ (Molecular Probe, Eugene, USA) in deionised distilled water (Molecular Probes, USA), 0.8× reaction buffer and cDNA template in low-profile 0.2 ml tube stripes (MJ Research, USA).

The PCR reactions and conditions that amplified very virulent and vaccine strain, UPM94/273 and D78, respectively, was optimized. It was found that the optimum concentration of SYBR Green I as labeling dye was 1 µl of 1:10³ diluted stocks. Real-time PCR profiles obtained from 2 µl of 1:10⁴ diluted SYBR Green I stock is not consistent (data not shown).

The amplification was performed in DNA Engine Opticon™ System (MJ Research, USA). No template control and tissue samples (bursa, thymus and ceacal tonsil) of uninfected SPF-chickens were used as negative control. PCR was performed with these conditions; 95° C. for 5 min then followed by 33 cycles of 94° C. for 30 sec, 60° C. for 20 sec and 72° C. for 40 sec then allowed the reaction to be incubated 82° C. to 85° C. before the fluorescence reading was taken. The fluorescence threshold limit of the DNA Engine Opticon™ System was set at 0.01.

A real-time PCR assay is also optimized by the number of cycle. It was found that amplification of mismatch PCR product occurred after 33 cycles. As shown in FIG. 2, the melting temperature (Tm) of the mismatch product was 86° C. to 87° C. whilst the Tm for the dimer product was 77° C.

Based on agarose gel electrophoresis (FIG. 2), a faint band of the expected size, 316 bp was observed with the formation of nonspecific dimer product. Lane M, 100 bp marker (Promega, USA), Lane 2, 3, 4 are triplicate of D78 with primer IF and IVIR.

Melting Curve Analysis

Upon completion of the amplification, the specificity of the amplified product was confirmed by melting curve analysis whereby the reaction was incubated by raising the incubation temperature from 72° C. to 99° C. in 0.4° C. increments with a hold of 1 second at each increment. The SYBR Green I fluorescence (F) was measured continuously during the heating period and the signal was plotted against temperature (T) to produce a melting curve for each sample. The melting peaks were then generated by plotting the negative derivative of the fluorescence over temperature versus the temperature (−dF/dT versus T). Since SYBR Green I dye binds to any dsDNA product, specificity and the absence of non-specific amplification were determined by determining the Tm of the non-specific product.

Development of the Real-Time PCR to Detect Very Virulent and Vaccine Strains of IBDV After establishing the optimum condition of the real-time PCR, the assay was performed on very virulent and attenuated vaccine strains, UPM94/273 and D78, respectively. The cDNA obtained from both strains were serially diluted and used as template in PCR using both match and mismatch primer combinations. FIG. 3 comprising FIGS. 3A, 3B, 3C, 3D and 3E depicting the amplification from 10-fold dilutions from $10^0$ to $10^{-5}$ of cDNA template of very virulent strain, UPM94/273 using match primer (IF & IVIR) and mismatch (IF & RCLA) primer combinations.

Figure 3B:
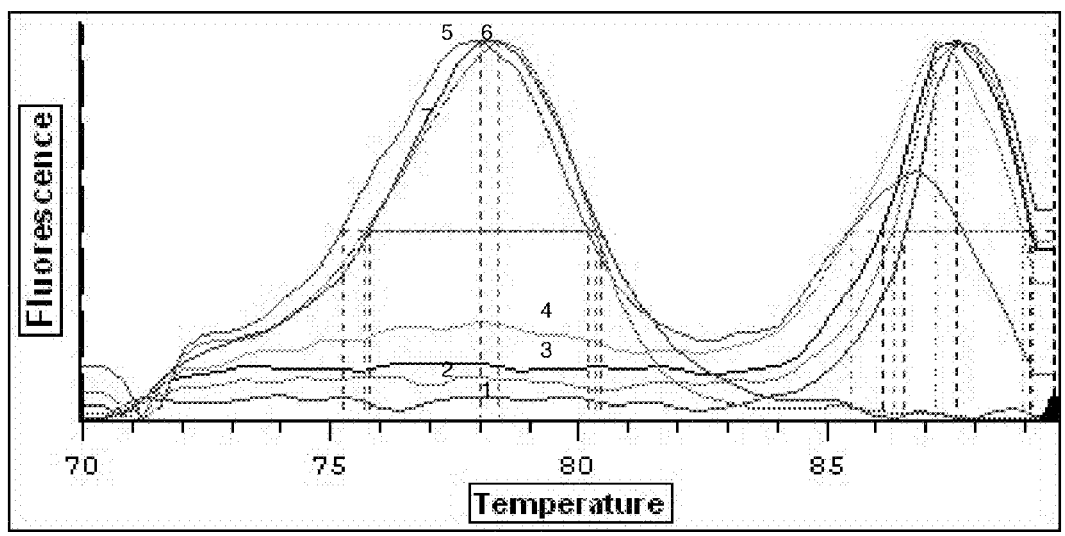
Figure 3C:
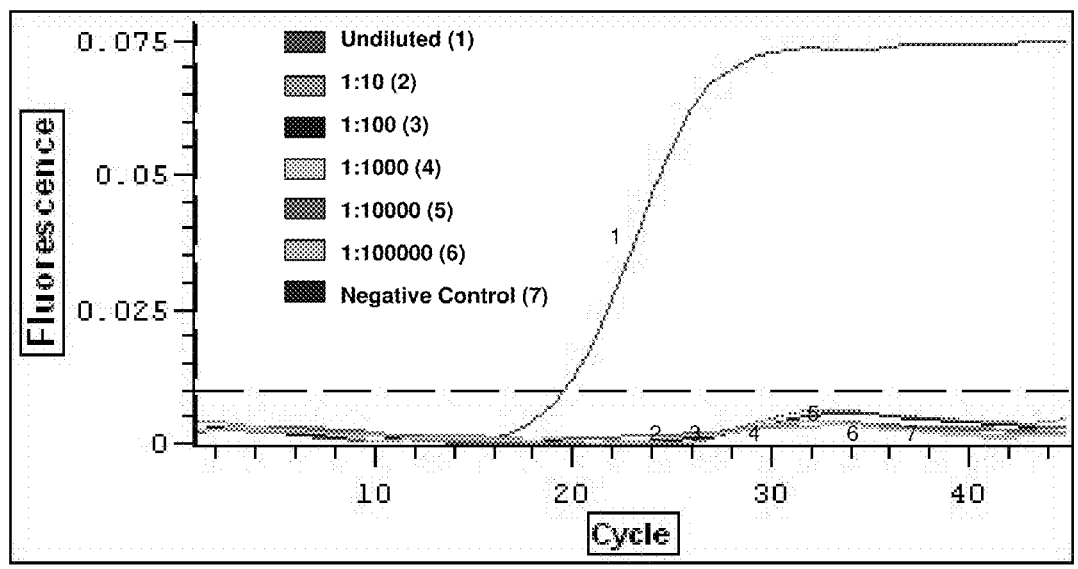
Figure 3D:
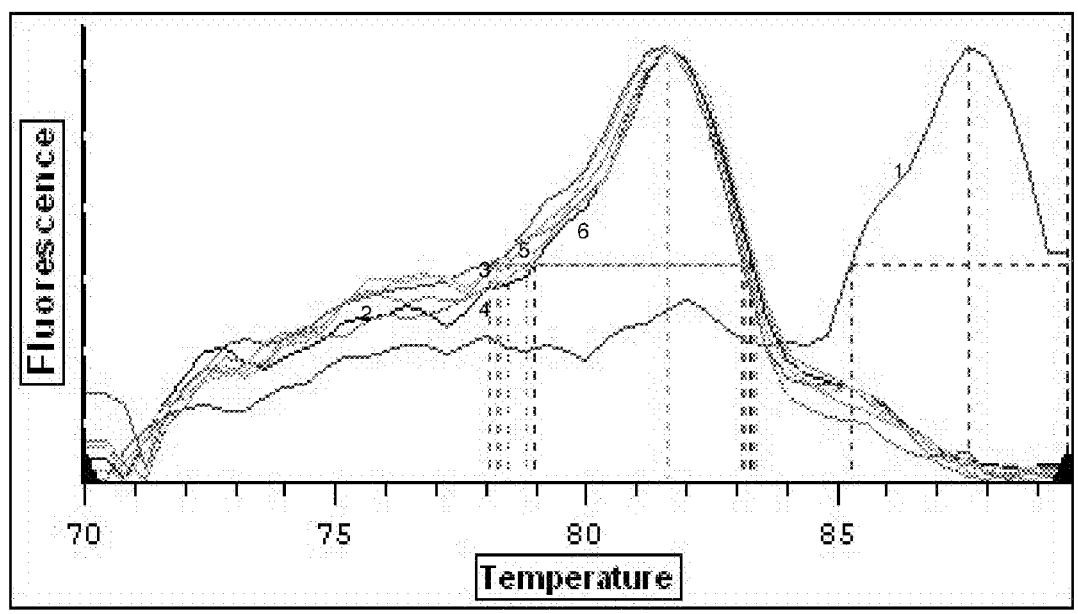

The RT product was generated from 12,000 ng/µl of total RNA. Amplification of specific PCR product using match primer was detected from undiluted (7,700 ng/µl) until $10^{-3}$ diluted (7.7 ng/µl) cDNA concentrations (FIG. 3A). However, amplification using mismatch primer was detected only from undiluted cDNA (FIG. 3C). The specificity of the amplification was also analyzed using melting curve analysis.

The melting temperature (Tm) of the amplicons obtained from undiluted cDNA until $10^{-3}$ diluted cDNA using match primer combinations was between 87.2° C. to 87.6° C. whilst the Tm for $10^{-4}$ to $10^{-5}$ diluted cDNA and negative control ranged from 78.0° C. to 78.4° C. (FIG. 3B). The melting curve analysis also showed that the mismatch primers produced a product with Tm of 87.6° C. from undiluted cDNA whilst the Tm for $10^{-1}$ until $10^{-5}$ diluted cDNA and negative control was 81.2° C. to 81.6° C. (FIG. 3D) (Table 4). Hence, the detection of specific amplification based on detection on Ct and Tm analysis was up to $10^{-3}$ diluted cDNA (7.7 ng/µl).

Figure 3E:
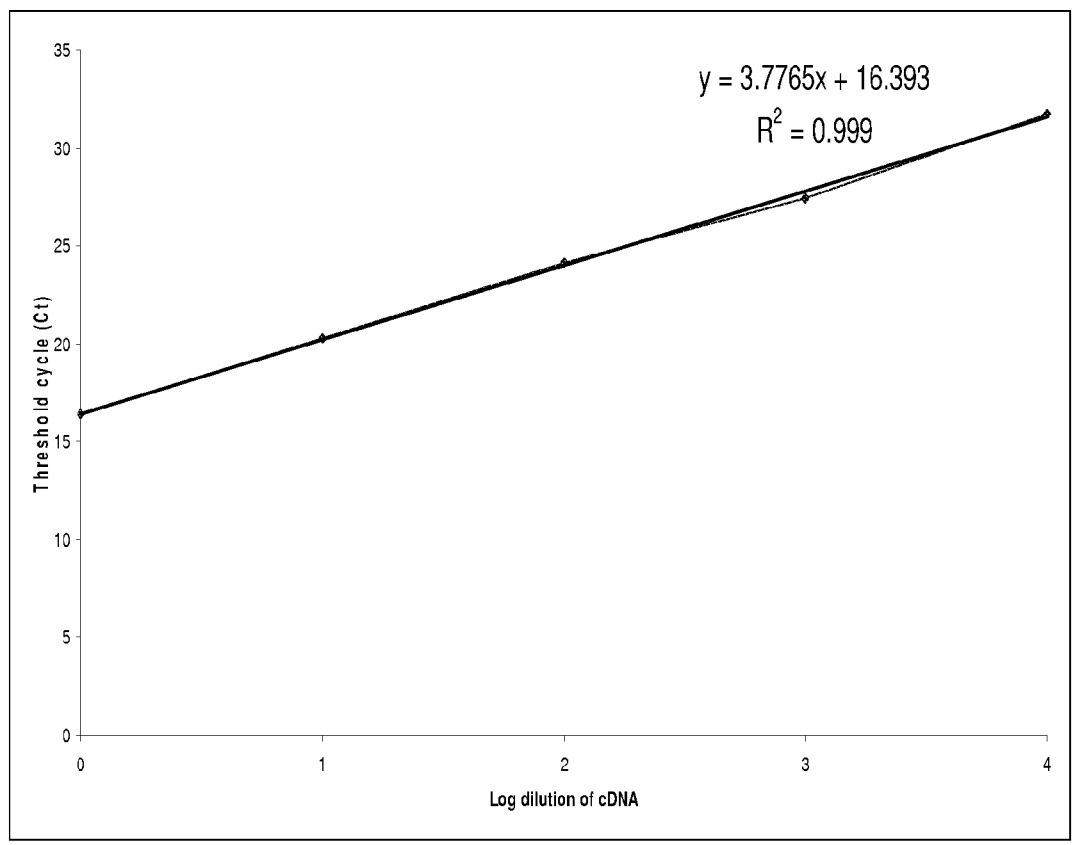

The correlation between the concentration of the cDNA and Ct values was analyzed by plotting a standard curve. As shown in FIG. 3E, Ct values can only be detected from amplification of undiluted to $10^{-4}$ diluted cDNA using match primer combination with a linear relationship between the amount of input cDNA and the Ct value from the amplification. The regression equation was Ct=3.7765 (log 10 dilution)+16.393 and $R^2$=0.999 (FIG. 3E). The Ct and Tm values obtained from amplification of serially diluted cDNA of very virulent IBDV strain UPM94/273 are summarized in Table 4 and 7, respectively.

Figure 4A:
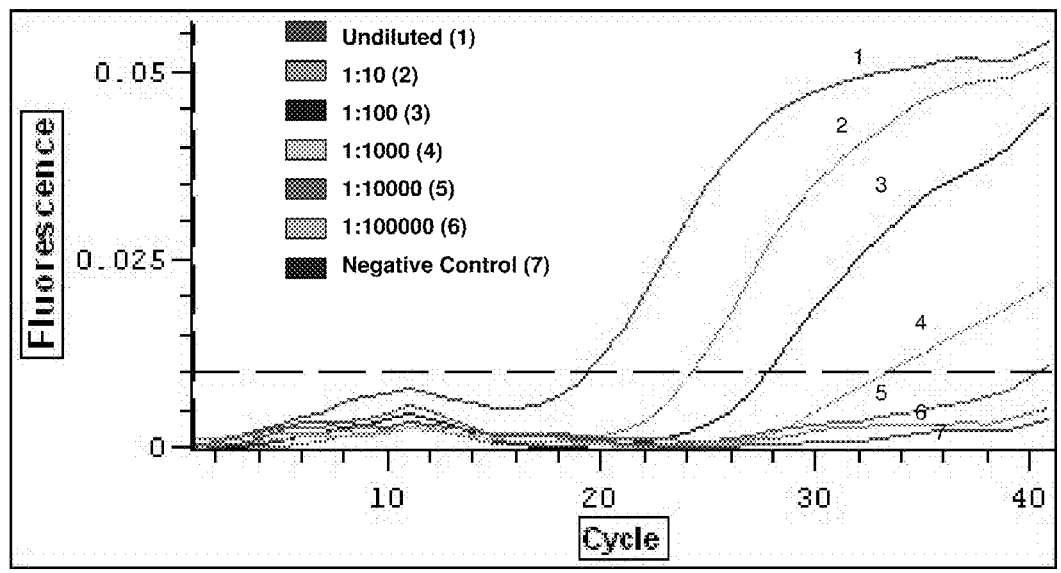
FIG. 4 depicts the performance of the real-time in detecting vaccine strain D78. Reverse transcription was generated from 6,500 to 7,000 ng/μl of total RNA. The real-time PCR was performed using 10-fold dilutions from $10^0$ to $10^{-5}$ (6,600 ng/μl to 0.066 ng/μl) of cDNA template (D78), match primer combination (primer IF & RCLA), mismatch primer combination (primer IF & IVIR), 1 μl of SYBR Green I (diluted 1:$10^3$) as labeling dye and fluorescence threshold limit was set at 0.01. Amplification of PCR product using match primer was detected from undiluted until $10^{-3}$ diluted cDNA whilst amplification using mismatch detected only from undiluted cDNA (FIGS. 4A and 4C). With match primer combinations, the products obtained from undiluted until $10^{-3}$ diluted cDNA produced a Tm ranged from 86° C. to 88° C. The Tm for $10^{-4}$ to $10^{-5}$ diluted cDNA and negative control was between 79° C. to 81° C.
(FIG. 4B). Melting curve analysis also showed that the mismatch primers produced a product with Tm of 87.6° C. from undiluted cDNA whilst the Tm for $10^{-1}$ until $10^{-5}$ diluted cDNA and negative control was between 76° C. to 78° C.
(FIG. 4D). A standard curve derived from 10-fold diluted cDNA of vaccine IBDV strain showed a linear relationship was observed between the amount of input cDNA and the Ct value. The regression equation was Ct=5.1279 (log 10 dilution)+19.433 and $R^2$=0.9809 (FIG. 4E).
Figure 4B:
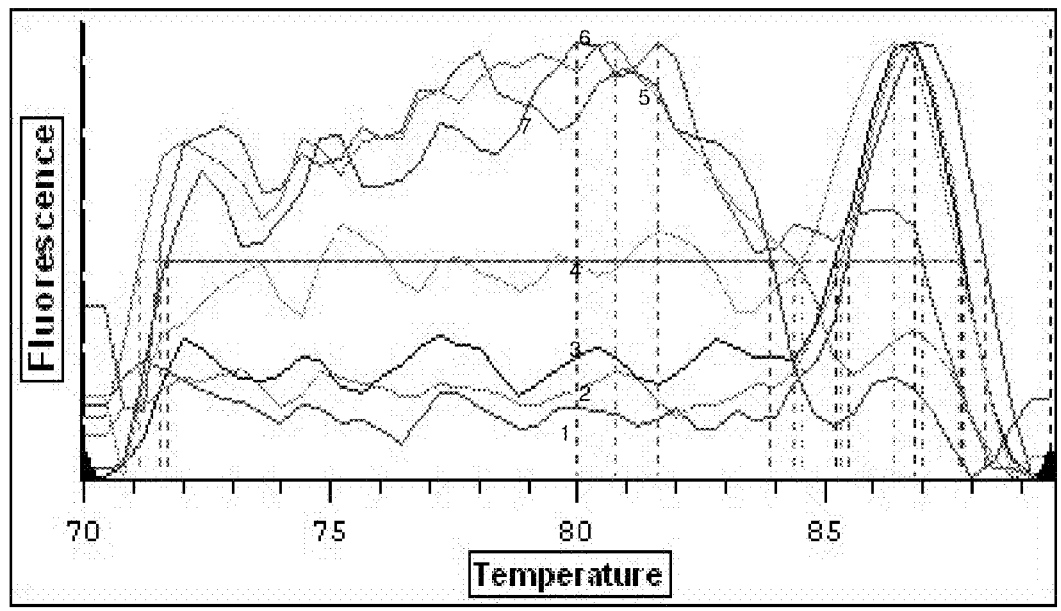
Figure 4C:
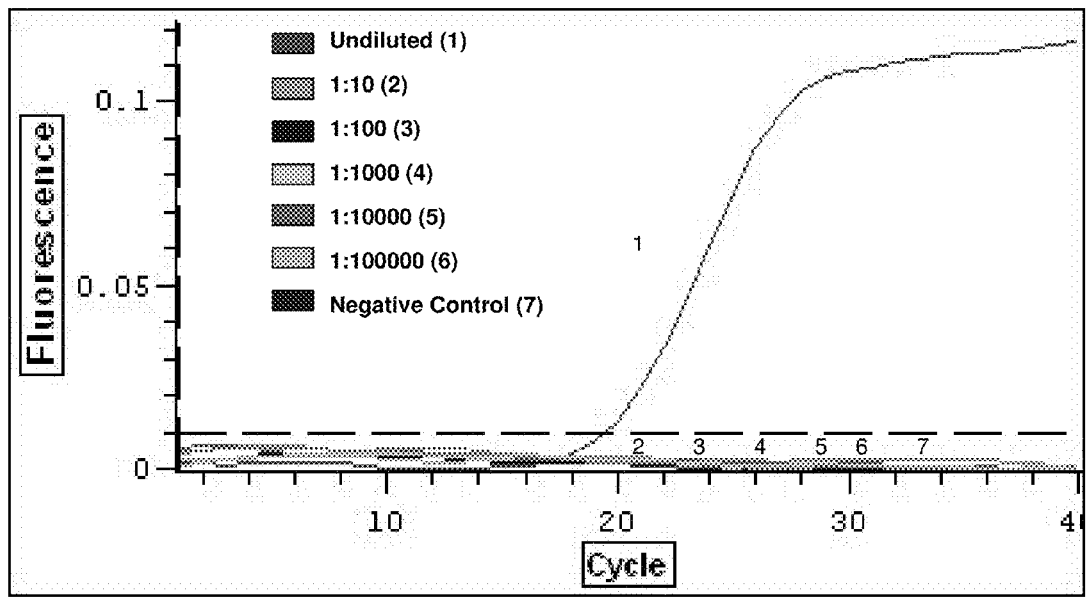
Figure 4D:
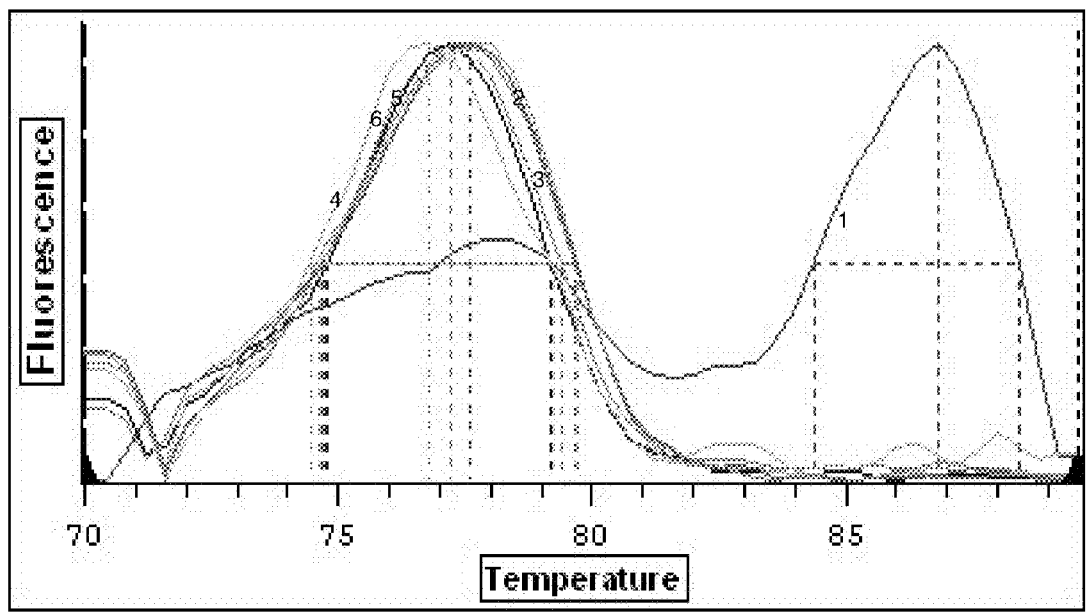

The performance of the real-time PCR in detecting vaccine strain IBDV was also analyzed and showed very similar as found for very virulent strain UPM94/273 (FIG. 4A to 4E). The RT product was generated from 6,500 to 7,000 ng/µl of total RNA. Amplification of PCR product using match primer was detected from undiluted (6,600 ng/µl) until $10^{-3}$ diluted (6.6 ng/µl) cDNA concentration (FIG. 4A). However, amplification using mismatch primer was detected only from undiluted cDNA (FIG. 4C).

Figure 4E:
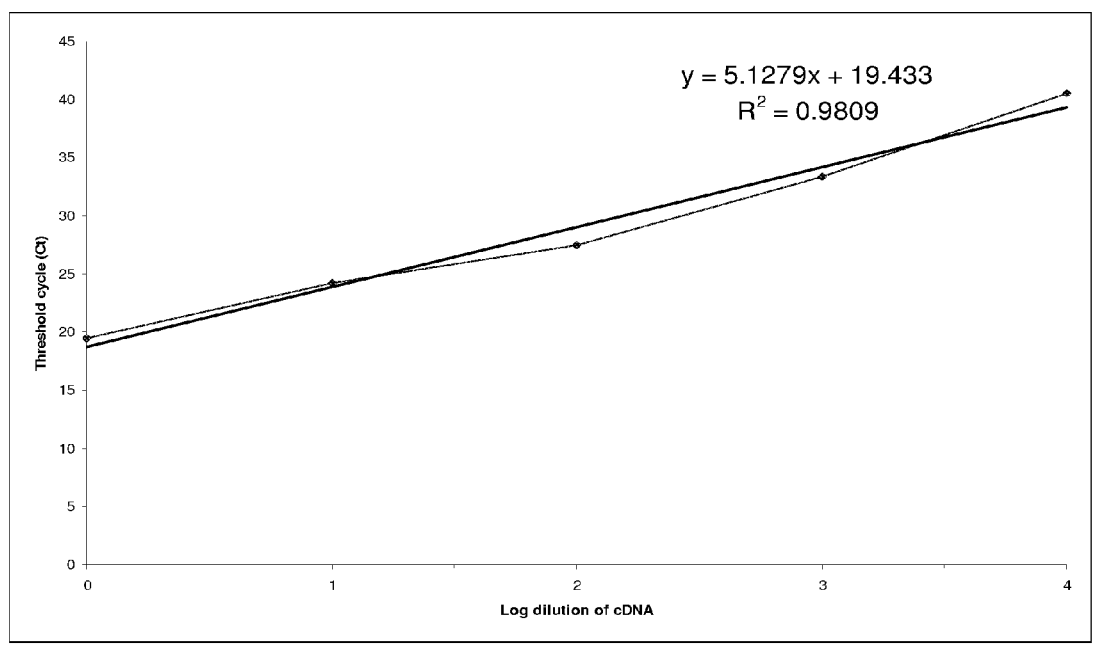

However, the Tm of the amplicons obtained from match primer combinations was between 86.4° C. to 86.8° C. whilst the Tm for $10^{-4}$ and $10^{-5}$ diluted cDNA as well as negative control ranged from 80.4° C. to 81.6° C. (FIG. 4B). The melting curve analysis also showed that the mismatch primers produced a product with Tm of 87.6° C. from undiluted cDNA whilst the Tm for $10^{-1}$ until $10^{-5}$ diluted cDNA and negative control was 77.2° C. to 77.6° C. (FIG. 4D) (Table 5). As shown in Table 5, Ct values can only be detected from amplification of undiluted to $10^{-4}$ diluted cDNA using match primers. However, the detection of specific amplification based on detection on Ct and Tm analysis was up to $10^{-3}$ diluted cDNA (6.6 ng/µl). A standard curve line was generated from amplification of the serially diluted vaccine strain, D78 by using match primer combination. As shown in FIG. 4E, a linear standard curve line was also observed between the serially diluted cDNA and the Ct value with the regression equation of Ct=5.1279 (log 10 dilution)+19.433 and $R^2$=0.9809 (FIG. 4E). The Ct and Tm values obtained from amplification of serially diluted cDNA of vaccine IBDV strain D78 are summarized in Table 5 and 8, respectively.

TABLE 4

Threshold cycle ($C_t$) and melting temperature (Tm) values of amplification of serially diluted cDNA of vvIBDV UPM94/273 using match and mismatch primer combinations.

| | Amplification using different primer combinations[a] | | | |
|---|---|---|---|---|
| | Primer IF & IVIR (Match) | | Primer IF & RCLA (Mismatch) | |
| cDNA dilution/ concentration | Ct value | Tm value (° C.) | Ct value | Tm value (° C.) |
| undiluted/7,700 ng/µl | 16.40 | 87.6 | 19.59 | 87.6 |
| 1:10¹/770 ng/µl | 20.41 | 87.6 | 0 | 81.6 |
| 1:10²/77 ng/µl | 24.10 | 87.6 | 0 | 81.6 |

TABLE 4-continued

Threshold cycle ($C_t$) and melting temperature (Tm) values of amplification of serially diluted cDNA of vvIBDV UPM94/273 using match and mismatch primer combinations.

| | Amplification using different primer combinations[a] | | | |
|---|---|---|---|---|
| | Primer IF & IVIR (Match) | | Primer IF & RCLA (Mismatch) | |
| cDNA dilution/ concentration | Ct value | Tm value (° C.) | Ct value | Tm value (° C.) |
| 1:10³/7.7 ng/μl | 27.45 | 87.2 | 0 | 81.6 |
| 1:10⁴/0.77 ng/μl | 31.70 | 78.0 | 0 | 81.2 |
| 1:10⁵/0.077 ng/μl | 0 | 78.4 | 0 | 81.6 |

[a]The real-time PCR was performed using 1 μl of SYBR Green I (diluted 1:10³) as labeling dye and the fluorescence threshold limit set at 0.01.

TABLE 5

Threshold cycle (Ct) and melting temperature (Tm) values of amplification of serially diluted cDNA of vaccine IBDV D78 using match and mismatch primer combinations.

| | Amplification using different primer combinations[a] | | | |
|---|---|---|---|---|
| | Primer IF & RCLA (Match) | | Primer IF & IVIR (Mismatch) | |
| cDNA dilution/ concentration | Ct value | Tm value (° C.) | Ct value | Tm value (° C.) |
| undiluted/6,660 ng/μl | 19.43 | 86.8 | 19.42 | 87.2 |
| 1:10¹/660 ng/μl | 24.27 | 86.8 | 0 | 77.2 |
| 1:10²/66 ng/μl | 27.72 | 86.8 | 0 | 77.2 |
| 1:10³/6.6 ng/μl | 33.34 | 86.4 | 0 | 77.6 |
| 1:10⁴/0.66 ng/μl | 40.53 | 81.6 | 0 | 77.6 |
| 1:10⁵/0.066 ng/μl | 0 | 80.4 | 0 | 77.2 |

[a]The real-time PCR was performed using 1 μl of SYBR Green I (diluted 1:10³) as labeling dye and the fluorescence threshold limit was set at 0.01.

Agarose Gel Electrophoresis Analysis

Figure 5A:
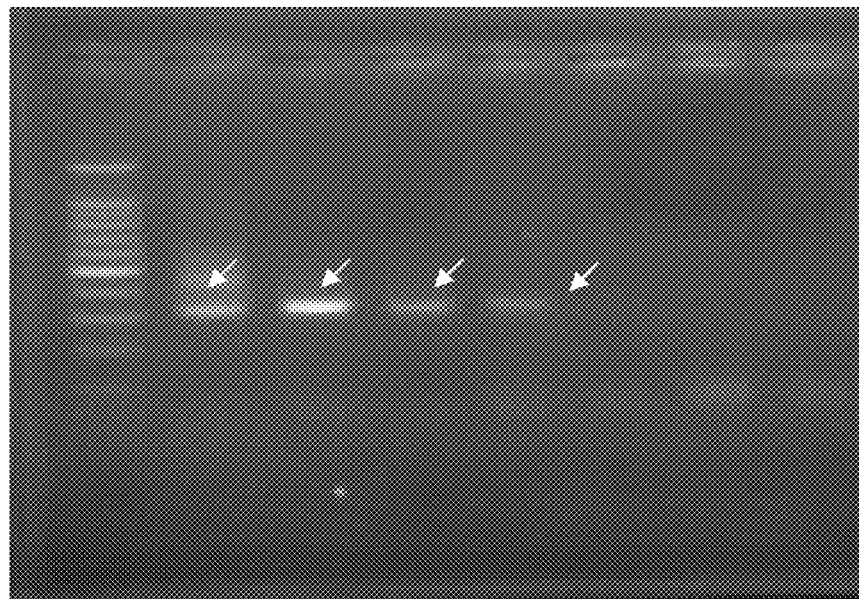
FIG. 5 shows agarose gel electrophoresis showing the specificity and detection limit of the PCR assay for cDNA from very virulent strain UPM94/273. The cDNA was diluted 10-fold from $10^0$ (7,700 ng/μl) to $10^{-5}$ (0.077 ng/μl) and used in amplification with match and mismatch primer combinations. Lane 1, 100 bp marker (Promega, USA); Lane 2, undiluted cDNA; Lane 3, $10^{-1}$ diluted cDNA; Lane 4, $10^{-2}$ diluted cDNA; Lane 5, $10^{-3}$ diluted cDNA; Lane 6, $10^{-4}$ diluted cDNA; Lane 7, $10^{-5}$ diluted cDNA; Lane 8, non-template negative control. Specific amplification of PCR product of the expected size 316 bp was observed from $10^0$ to $10^{-3}$ diluted cDNA with match primer combination only (arrow) (FIG. 5A). A faint nonspecific amplification was observed from amplification of undiluted cDNA sample using mismatch primer (FIG. 5B). No specific amplification was observed from the serially diluted cDNA and non-template negative control when amplification was performed using mismatch primer combination (FIG. 5B).
Figure 5B:
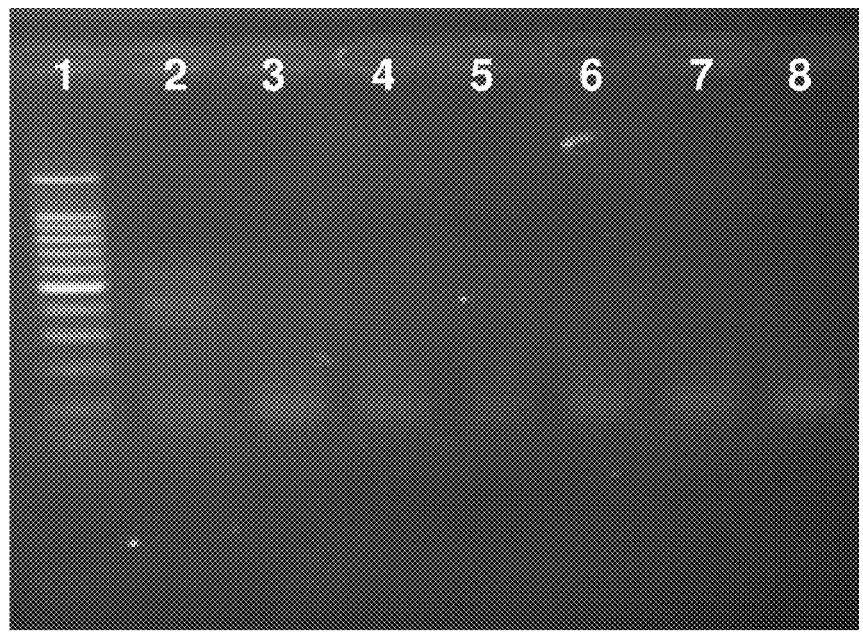

Amplification of the real-time PCR products was also verified on 1.7% agarose gel in TAE buffer. The size of the product was estimated using 100 bp DNA ladder (Promega, USA). The specificity and detection limit of the PCR using different primer combinations in detecting very virulent and vaccine strains IBDV were also confirmed by agarose gel electrophoresis. Specific amplification of PCR product of the expected size 316 bp was observed from 10⁰ to 10⁻³ diluted cDNA of UPM94/273 with match primer combination only (FIG. 5A). Nonspecific product was observed only from amplification of undiluted cDNA sample. In the case of mismatch primer combination, no amplification was detected except for nonspecific PCR products (~400 base pair and ~600 base pair) were observed from undiluted cDNA sample (FIG. 5B).

Figure 6A:
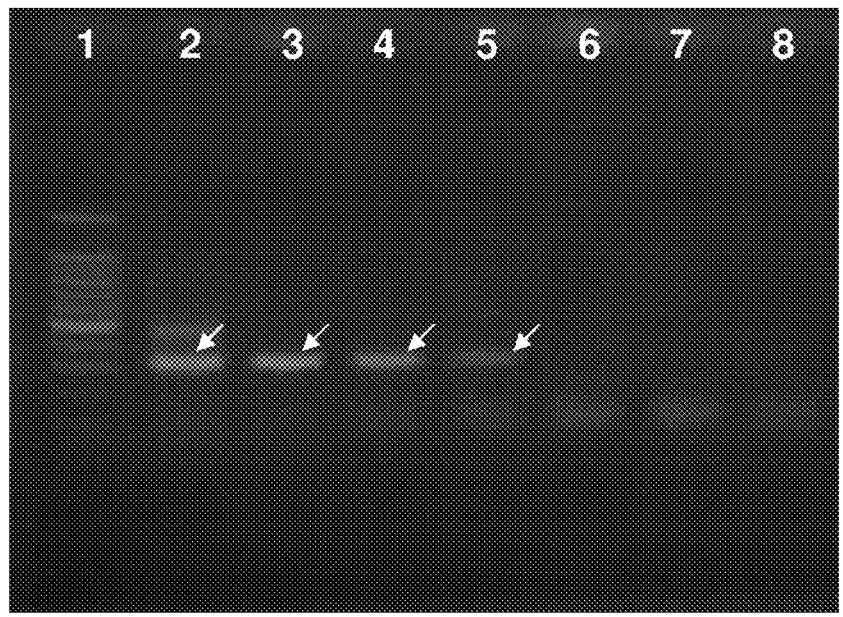
FIG. 6 shows agarose gel electrophoresis showing the specificity and detection limit of the PCR assay for cDNA from vaccine strain D78. The cDNA was diluted 10-fold from $10^0$ (6,600 ng/μl) to $10^{-5}$ (0.066 ng/μl) and used in amplification with match and mismatch primer combinations. Lane 1, 100 bp marker (Promega, USA); Lane 2, undiluted cDNA; Lane 3, $10^{-1}$ diluted cDNA; Lane 4, $10^{-2}$ diluted cDNA; Lane 5, $10^{-3}$ diluted cDNA; Lane 6, $10^{-4}$ diluted cDNA; Lane 7, $10^{-5}$ diluted cDNA; Lane 8, non-template negative control. Specific amplification (arrow) was observed from $10^0$ to $10^{-3}$ diluted cDNA with match primer combination only (FIG. 6A). A faint band of the nonspecific amplification was also observed from amplification of undiluted cDNA sample using mismatch primer (FIG. 6B). No specific amplification was observed from the serially diluted cDNA and non-template negative control when amplification was performed using mismatch primer combination (FIG. 6B).
Figure 6B:
Figure 7A:
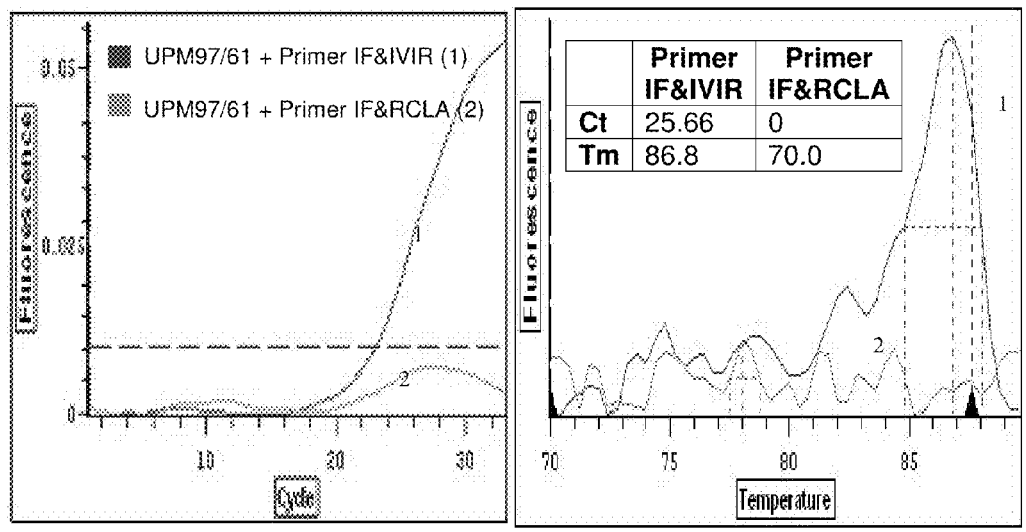
FIG. 7 depicts the performance of the real-time in detecting specific amplification of vvIBDV (UPM97/61 and UPM94/273) and attenuated vaccine (D78, LZD, TAD and IBDVAC) strains.
Figure 7B:
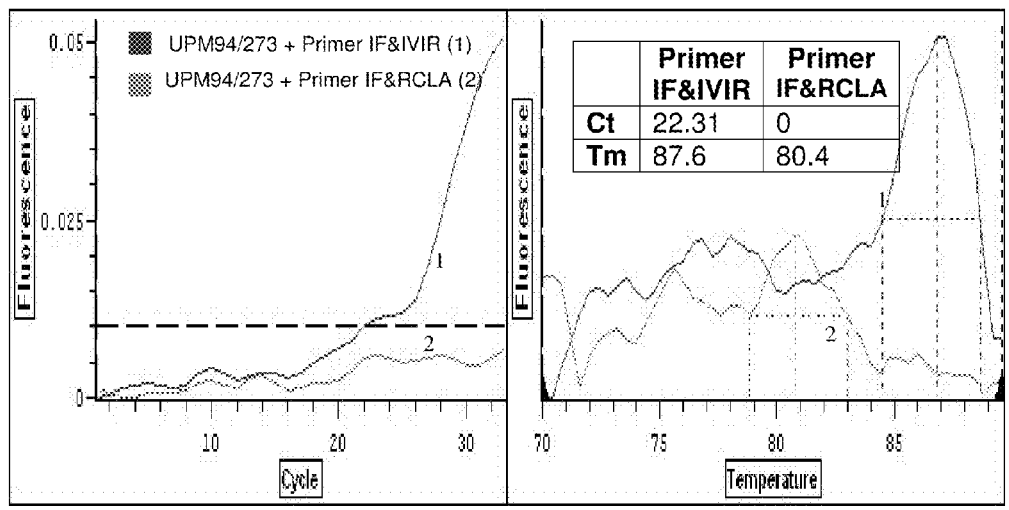
Figure 7C:
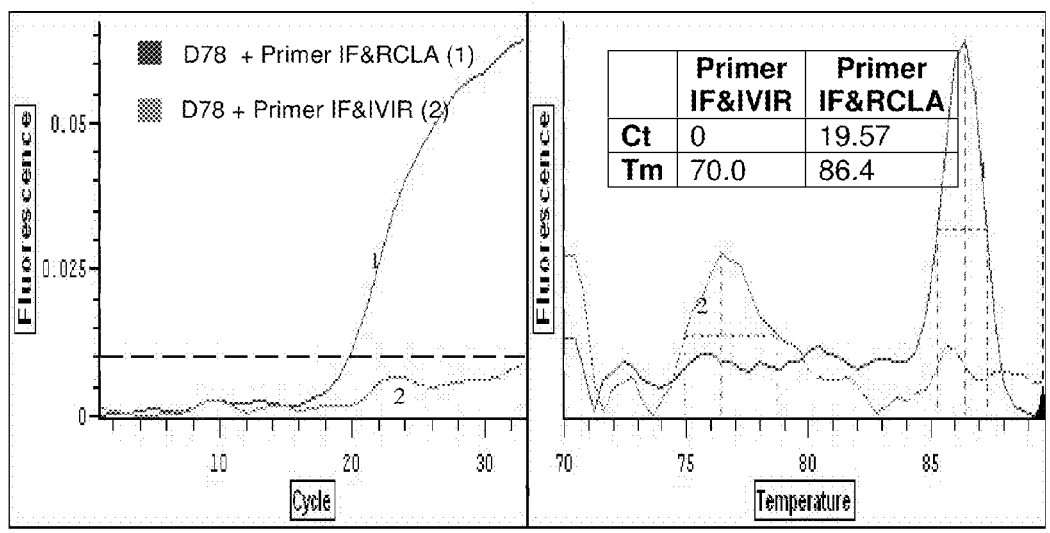
Figure 7D:
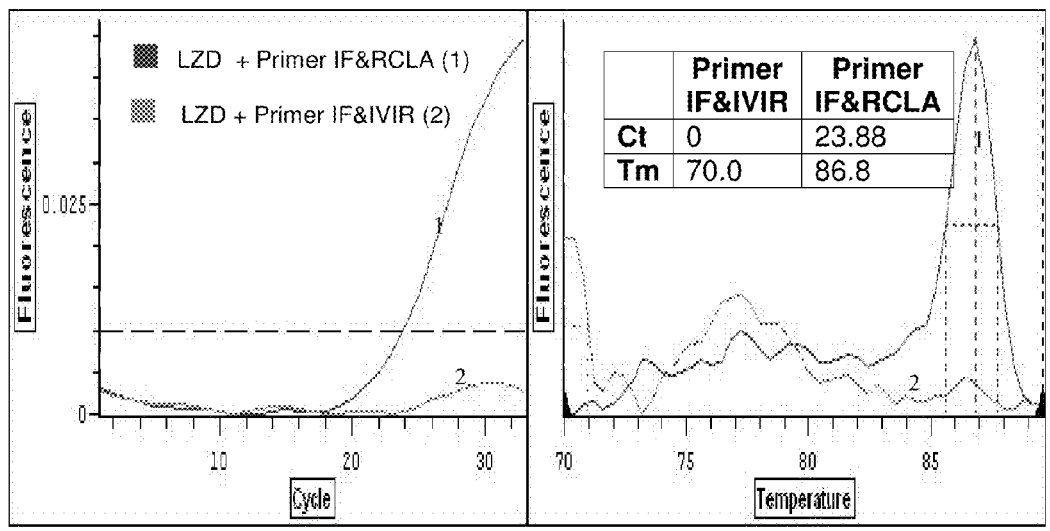
Figure 7E:
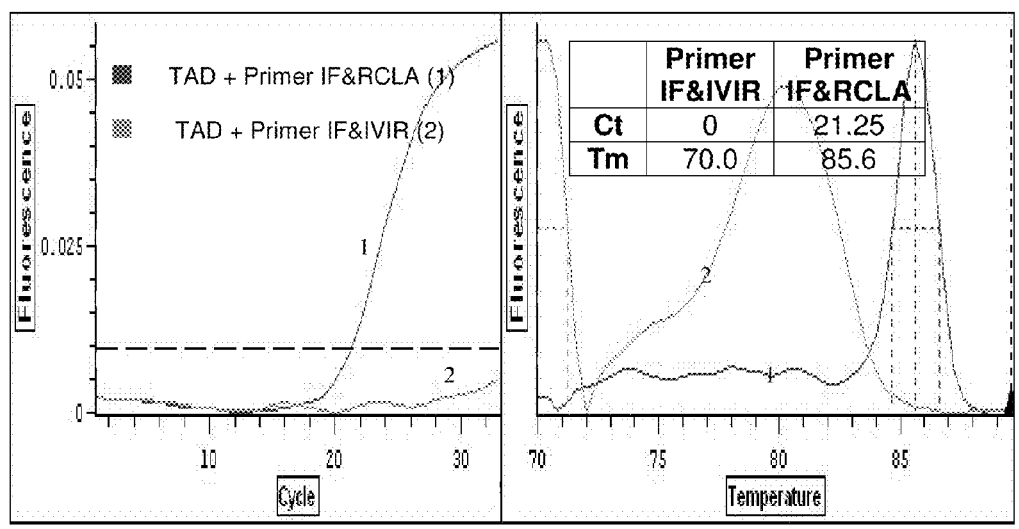
Figure 7F:
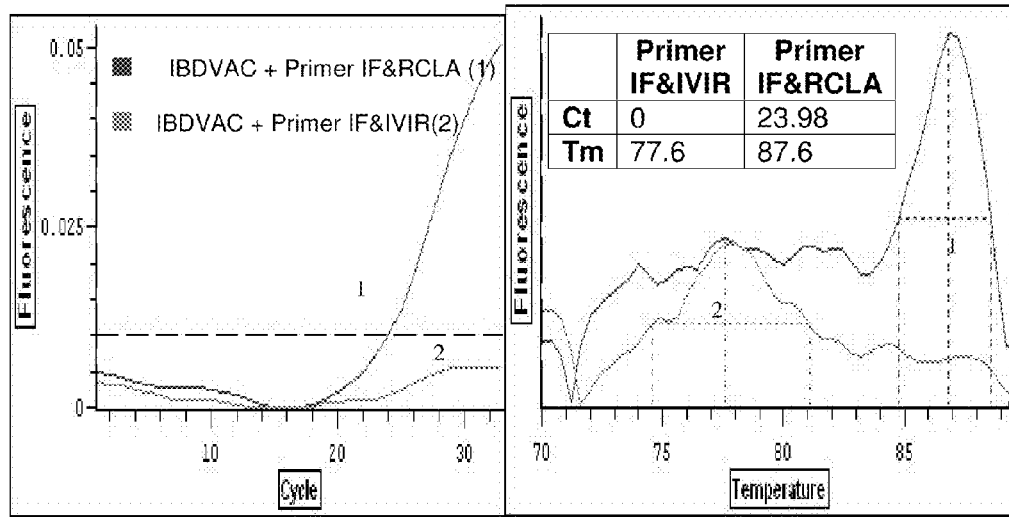

Similar results were obtained when the PCR products from D78 were analyzed on 1.7% agarose gel. A PCR product of the expected size (316 bp) was observed from 10⁰ to 10⁻³ diluted cDNA using match primer combination only (FIG. 6A). When the serially diluted cDNA were tested using mismatch primer combinations, nonspecific amplification was detected only from the undiluted cDNA whilst, no amplification was detected from the diluted cDNA samples (FIG. 6B).

Evaluation of the Real-Time PCR

After establishing the real-time PCR condition and the detection limits for the detection of very virulent and vaccine strains, UPM94/273 and D78, respectively, the assay was also performed on other IBDV isolates as listed in Table 1. The real-time PCR was performed using both match and mismatch primer combinations and the total RNA concentration ranging from 4,500 to 12,800 ng/μl. The real-time PCR was also tested using tissue samples such as bursa, thymus and ceacal tonsil of control uninfected SPF-chickens. As shown in Table 6, no Ct values were generated from amplification of the control negative tissue samples and the Tm values were in the ranged of 72.0° C. to 79.6° C.

However, as expected the match primer combinations amplified the UPM94/273 sample. No specific amplifications were detected from those tissue samples using both match and mismatch primers (FIG. 9). However, the cDNA concentration was set at 4000 ng/μl. The amplification profiles of the real-time PCR assay for the amplification of IBDV strains UPM97/61, UPM94/273, D78, Delvax LZD, TAD Gumboro and IBDVAC were shown in FIGS. 7A, 7B, 7C, 7D, 7E and 7F, respectively. Regardless of the IBDV isolates, the specific amplification was detected only from match primer combination with the Ct value of the amplified products ranged from 19 to 28 and the Tm of the amplified products ranged from 86° C. to 88° C. for both cDNA obtained from very virulent and vaccine strains.

The very virulent strains, UPM94/273 and UPM97/61 were amplified only with the match primer (primer IF & IVIR) whilst the vaccine strains, D78, Delvax LZD, TAD Gumboro and IBDVAC were amplified only with match primer (primer IF & RCLA). No amplification with Ct value 0 was detected for amplification of the IBDV using mismatch primer combinations.

Figure 8:
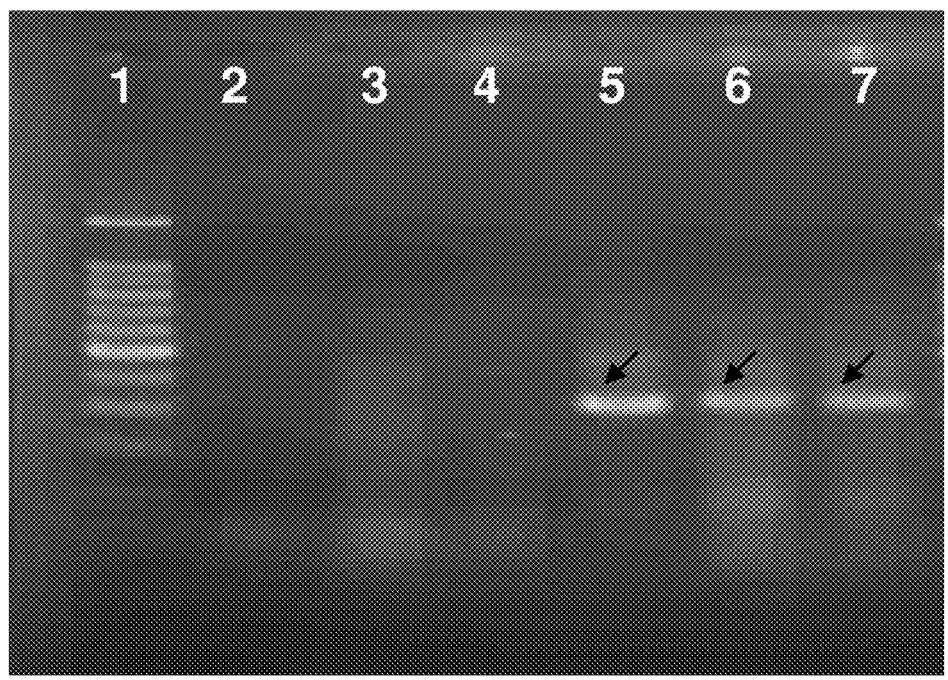
FIG. 8 shows agarose gel electrophoresis showing the specificity of the real-time PCR assay in detecting vaccine strains; TAD, LZD and IBDVAC using both match and mismatch primer combinations. The real-time PCR was performed using 4,000 ng/μl of cDNA. Lane 1, 100 bp marker (Promega, USA); Lane 2, TAD Gumboro with mismatch primer; Lane 3, Delvax LZD with mismatch primer; Lane 4, IBDVAC with mismatch primer; Lane 5, TAD Gumboro with match primer; Lane 6, Delvax LZD with match primer and Lane 7, IBDVAC with match primer. PCR product with the expected size 316 bp (arrow) was observed only with match primer combination.

The specific amplification of the vaccine strains, Delvax LZD, TAD Gumboro and IBDVAC using match and mismatch primer combination were also verified using 1.7% agarose gel. As shown in FIG. 8, specific amplification of PCR product of the expected size (316 bp) was detected only from match primer but not mismatch primer combinations.

TABLE 6

Threshold cycle (Ct) and melting temperature (Tm) values of amplification of negative control samples.

| | Primer IF & IVIR | | Primer IF & RCLA | |
|---|---|---|---|---|
| Samples[a] | Ct | Tm (° C.) | Ct | Tm (° C.) |
| UPM94/273 (positive control) | 19.158 | 88.0 | None | 72.0 |
| Bursa | None | 78.8 | None | 72.0 |
| Thymus | None | 79.6 | None | 79.6 |
| Cecal tonsil | None | 79.2 | None | 79.6 |

[a]The concentration of the undiluted cDNA was 4000 ng/μl.

TABLE 7

Detection of signatory threshold cycle (Ct) values of very virulent and vaccine strains IBDV using different primer combinations.

| | | Threshold cycle (Ct) value[a] | |
|---|---|---|---|
| Isolates | Strains | Primer IF & IVIR | Primer IF & RCLA |
| UPM97/61 | very virulent | 19 to 28 | >29 or 0 |
| UPM94/273 | very virulent | 19 to 28 | >29 or 0 |
| D78 | vaccine | >29 or 0 | 19 to 28 |

TABLE 7-continued

Detection of signatory threshold cycle (Ct) values of very virulent and vaccine strains IBDV using different primer combinations.

| | | Threshold cycle (Ct) value[a] | |
|---|---|---|---|
| Isolates | Strains | Primer IF & IVIR | Primer IF & RCLA |
| TAD Gumboro | vaccine | >29 or 0 | 19 to 28 |
| Delvax Gumboro LZD | vaccine | >29 or 0 | 19 to 28 |
| IBDVAC | vaccine | >29 or 0 | 19 to 28 |

[a]The real-time PCR was performed using 4000 ng/µl of cDNA, 1 µl of SYBR Green I (diluted 1:10³) as labeling dye and the fluorescence threshold limit was set at 0.01.

The SYBR Green I based real-time PCR detects both very virulent and vaccine strain IBDV as detected based on the Ct and Tm values. However, the detection based on Tm has lower CV value, 0.87 compared to Ct with a CV of 9.58 (Table 9). This suggests that Tm is a consistent parameter in detecting specific amplification. The high CV for Ct values are expected since the absolute quantity of the viral RNA in the samples may be different. It has been showed that the initial copy number of targeted sequences in the template significantly influencing the Ct values (Mackay et al., 2002).

TABLE 8

Detection of signatory melting temperature (Tm) values from very virulent and vaccine strains IBDV using different primer combinations.

| | | Melting temperature (Tm) values (° C.)[a] | |
|---|---|---|---|
| Isolates | Strains | Primer IF & IVIR | Primer IF & RCLA |
| UPM97/61 | very virulent | 86 to 88 | <80 |
| UPM94/273 | very virulent | 86 to 88 | <80 |
| D78 | vaccine | <80 | 86 to 88 |
| TAD Gumboro | vaccine | <80 | 86 to 88 |
| Delvax Gumboro LZD | vaccine | <80 | 86 to 88 |
| IBDVAC | vaccine | <80 | 86 to 88 |

[a]The real-time PCR was performed using 4000 ng/µl of cDNA, 1 µl of SYBR Green I (diluted 1:10³) as labeling dye and the fluorescence threshold limit set at 0.01.

TABLE 9

Intra-assay variation of Ct and Tm values of real-time PCR using match primer combination in detecting very virulent and vaccine strains of IBDV

| Threshold cycle (Ct) | | | | Melting temperature (Tm) | | | |
|---|---|---|---|---|---|---|---|
| Interval | Range | Mean ± SD | CV | Interval | Range | Mean ± SD | CV |
| 19.57-25.66 | 6.09 | 22.775 ± 2.18 | 9.58 | 85.6-87.6 | 2.00 | 86.8 ± 0.759 | 0.87 |

CV = coefficient variations
SD = standard deviations

Purification of PCR Products

The expected PCR products (~593 bp) generated from primers, FVVC and RVVC were purified by using GENECLEAN (BIO 101, USA) following the manufacturer's instructions. Briefly, the PCR products were cut from the agarose gel by scalpel blade and the weight of the each excised band was measured. Three volumes (three times the weight of the gel) of Sodium Iodine (NaI) was added and incubated at 45° C.-55° C. water bath for 5 min until all of the gel dissolved. The glass milk (containing insoluble silica matrix) was vortex vigorously for 1 min. Approximately 5 µl of glass milk was added for each tube (solution containing 5 µg or less DNA) and mixed well, incubated for 5 min at room temperature and mixed every 1-2 min to allow binding of the DNA to the silica matrix.

The silica matrix with the bound DNA was then pelleted in a microcentifuge for 5 secs at full speed. The pellet was then washed three times with 10-15 volume (approximately 500 µl) New Wash buffer. The pellet was resuspended in the wash by pipetting back and forth while digging into the pellet with the pipet tip and centrifuged at 13000 rpm for 5 sec at 4° C. After the third wash, the last bit of liquid was removed by centrifuged the tube again for a few seconds, the pellet was allowed to dry at RT (5 to 10 min). The DNA was eluted from the glass milk by resuspending the white pellet with 10 µl of sterile dH2O, centrifuged at 13000 rpm for 1 min. The yield of the eluted DNA was estimated by agarose gel electrophoresis.

DNA Sequencing

The yield of the eluted DNA was estimated by agarose gel electrophoresis. The purified products obtained from PCR amplification from very virulent and vaccine strains were sequenced using primers IF & IVIR and primers IF & RCLA, respectively (Table 2). Each PCR product was sequenced twice from both directions. The sequencing was carried out using ABI PRISM® BigDye Terminator Cycle Sequencing Ready Reaction Kit v2.0 (Perkin Elmer, USA) in an automated DNA sequencer (ABI PRISM® 377 DNA Sequencer) following the instructions supplied by the manufacturer. The cycle sequencing was conducted with the following thermal cycle profiles; 30 cycles, each with 96° C. for 10 seconds, 50° C. for 5 seconds, and 60° C. for 4 minutes.

Sequence Analysis of the PCR Amplified Product

Figure 10:
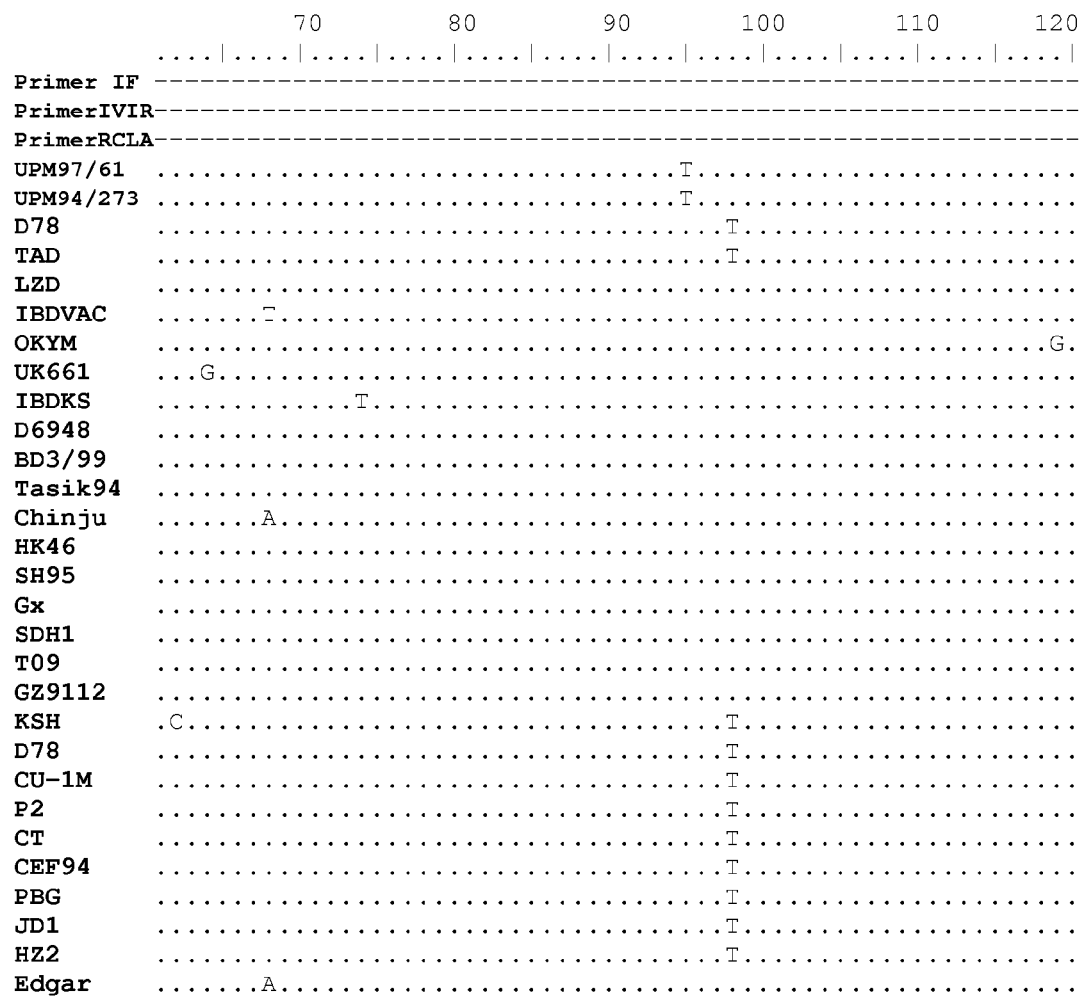
FIG. 10 shows nucleotide sequences (316 bp) of UPM94/273, UPM97/61, D78, LZD, TAD and IBDVAC used in this study. The nucleotide sequences of primers IF, IVIR and RCLA are also given (SEQ ID NOs:3-5). The nucleotide sequence of primer IF corresponds to SEQ ID NO:3. The nucleotide sequences of primers IVIR and RCLA depicted in FIG. 10 correspond to the reverse complement sequences of SEQ ID NO:4 and SEQ ID NO:5 respectively. The nucleotide sequences encompassed from position 1835 to 2133 of the VP4 region.

As shown in FIG. 10, a total of 316 bp sequences encompassing the VP4 gene from position 1835 to 2133 of the PCR products of UPM94/273, UPM97/61, D78, Delvax LZD, TAD Gumboro and IBDVAC were characterized. The nucleotide sequences of primer FVVC, VVC, IF, IVIR and RCLA were also given. The sequences of the match primers were conserved when compared to the respective isolates except for the vaccine strain, IBDVAC. IBDVAC has two nucleotide variations each on primer IF and RCLA. At primer IF, the nucleotide variation is at position 1851 from A to T whilst at primer RCLA, the variation is at position 2141 from C to T (FIG. 10).

The invention claimed is:

1. A diagnostic assay kit adapted or assembled to perform a method of detecting Infectious Bursal Disease Virus (IBDV) strains in a chicken or other bird sample, comprising: at least one oligonucleotide primer pair, wherein said oligonucleotide primer pair consists of SEQ ID NO:1 and SEQ ID NO:2.

2. The diagnostic assay kit of claim 1, further comprising reagents for reverse transcribing into cDNA an RNA sample from a chicken or other bird that is infected with IBDV strains to be distinguished.

3. The diagnostic assay kit of claim 1, further comprising reagents for amplifying said IBDV strains by means of a polymerase chain reaction (PCR) using the oligonucleotide primer pair.

4. The diagnostic assay kit of claim 3, wherein said PCR is real-time (RT)-PCR.

5. The diagnostic assay kit of claim 3, wherein the PCR produces an amplified product in the size of 593 base pair (bp).

6. The diagnostic assay kit of claim 1, further comprising SYBR Green I.

7. The diagnostic assay kit of claim 1, further comprising reagents for isolating said IBDV strains in the sample.

8. The diagnostic assay kit of claim 1, wherein one of said IBDV strains is selected from the group consisting of very virulent strains UPM97/61 and UPM 94/273.

9. The diagnostic assay kit of claim 1, wherein one of said IBDV strains is selected from the group consisting of vaccine strains D78, TAD Gumboro, Delvax Gumboro LZD, and IBDVAC.

10. The diagnostic assay kit of claim 1, further comprising reagents for diluting cDNA from said IBDV strain(s).

11. The diagnostic assay kit of claim 1, wherein the diagnostic assay kit differentiates between very virulent IBDV strains and vaccine IBDV strains.

12. A diagnostic assay kit adapted or assembled to perform a method of distinguishing between Infectious Bursal Disease Virus (IBDV) strains in a chicken or other bird sample, comprising: at least one oligonucleotide primer pair, wherein said oligonucleotide primer pair consists of SEQ ID NO:3 and SEQ ID NO:4 or SEQ ID NO:3 and SEQ ID NO:5.

13. The diagnostic assay kit of claim 12, further comprising reagents for reverse transcribing into cDNA an RNA sample from a chicken or other bird that is infected with IBDV strains to be distinguished.

14. The diagnostic assay kit of claim 12, further comprising reagents for amplifying said IBDV strains by means of a polymerase chain reaction (PCR) using the at least one oligonucleotide primer pair.

15. The diagnostic assay kit of claim 14, wherein said PCR is real-time (RT)-PCR.

16. The diagnostic assay kit of claim 14, wherein the PCR produces an amplified product in the size of 361 base pair (bp).

17. The diagnostic assay kit of claim 14, further comprising reagents for distinguishing said IBDV strains based on melting temperature (Tm) values of a nucleic acid product of the PCR amplification.

18. The diagnostic assay kit of claim 12, further comprising SYBR Green I.

19. The diagnostic assay kit of claim 12, further comprising reagents for isolating said IBDV strains in the sample.

20. The diagnostic assay kit of claim 12, wherein the diagnostic assay kit distinguishes very virulent strain UPM 94/273 and other IBDV strains that have nucleotide sequence complementary to SEQ ID NO:3 and SEQ ID NO:4.

21. The diagnostic assay kit of claim 12, wherein the diagnostic assay kit distinguishes vaccine strain D78 and other IBDV strains that have nucleotide sequence complementary to SEQ ID NO:3 and SEQ ID NO:5.

22. The diagnostic assay kit of claim 12, further comprising reagents for diluting cDNA from said IBDV strain(s).

23. The diagnostic assay kit of claim 22, wherein said diluted cDNA from very virulent strains is diluted from at least $10^0$ to $10^{-5}$ fold.

24. The diagnostic assay kit of claim 22, wherein said diluted cDNA from vaccine strains is diluted from at least $10^0$ to $10^{-5}$ fold.

25. A diagnostic assay kit adapted or assembled to perform a method for detecting and/or differentiating IBDV in chicken or bird samples, comprising: oligonucleotide primer pairs consisting of SEQ ID NO:1 and SEQ ID NO:2, SEQ ID NO:3 and SEQ ID NO:4 or SEQ ID NO:3 and SEQ ID NO:5.

* * * * *